(12) United States Patent
Yoo et al.

(10) Patent No.: US 10,125,194 B2
(45) Date of Patent: Nov. 13, 2018

(54) DUAL TARGETING ANTIBODY OF NOVEL FORM, AND USE THEREOF

(75) Inventors: Jin San Yoo, Daejeon-si (KR); Weon Sup Lee, Daejong-si (KR); Sung Woo Kim, Daejeon-si (KR); Sang Ryeol Shim, Daejeon-si (KR)

(73) Assignee: PHARMABCINE INC., Daejeon-si (KR)

( * ) Notice: Subject to any disclaimer, the term of this patent is extended or adjusted under 35 U.S.C. 154(b) by 978 days.

(21) Appl. No.: 13/319,899

(22) PCT Filed: Jul. 22, 2009

(86) PCT No.: PCT/KR2009/004084
§ 371 (c)(1),
(2), (4) Date: Nov. 10, 2011

(87) PCT Pub. No.: WO2010/134666
PCT Pub. Date: Nov. 25, 2010

(65) Prior Publication Data
US 2012/0065380 A1 Mar. 15, 2012

(30) Foreign Application Priority Data
May 20, 2009 (KR) ........................ 10-2009-0044032

(51) Int. Cl.
*A61K 39/395* (2006.01)
*C12P 21/08* (2006.01)
*C07K 16/00* (2006.01)
*C07K 16/28* (2006.01)

(52) U.S. Cl.
CPC ...... *C07K 16/2863* (2013.01); *C07K 2317/76* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 5,942,602 A * | 8/1999 | Wels | ................ | A61K 47/48561 424/1.49 |
| 6,342,219 B1 * | 1/2002 | Thorpe et al. | ............. | 424/145.1 |
| 7,090,843 B1 | 8/2006 | Francisco | | |
| 9,150,650 B2 * | 10/2015 | Yoo | ..................... | C07K 16/2863 |
| 2005/0244901 A1 * | 11/2005 | Peschen | ................. | C07K 16/14 435/7.31 |
| 2009/0111146 A1 | 4/2009 | Ohtsuka | | |
| 2014/0302039 A1 * | 10/2014 | Jeong | ..................... | C07K 16/22 424/138.1 |

FOREIGN PATENT DOCUMENTS

| | | |
|---|---|---|
| EP | 1179541 | 2/2002 |
| WO | WO1993/23550 | 11/1993 |
| WO | WO2004/076485 | 9/2004 |
| WO | WO 2006/005361 | 1/2006 |
| WO | WO2008/090958 | 7/2008 |
| WO | WO 2008/153237 | 12/2008 |

OTHER PUBLICATIONS

Bremer et al (Journal of Biological Chemistry, 2005, 280:10025-10033).*
McGrath (Journal of Neuroscience Research, 1997, 47:123-133).*
Sofroniew (Annual Review of Neuroscience, 2001, 24:1217-1281).*
Daniels et al. (Clinical Immunology, 2006, 121:144-158).*
Ortiz-Sanchez (Vaccines and Antibodies, 2008, 8:609-632).*
Makabe et al. (Biochemical and Biophysical Research Communications, 2005, 328:98-105).*
Rudikoff et al. (Proceedings of the National Academy of Sciences, 1982, 79:1979-1983).*
MacCallum et al. (Journal of Molecular Biology, 1996, 262:732-745).*
De Pascalis et al. (Journal of Immunology, 2002, 169:3076-3084.*
Casset et al. (Biochemical and Biophysical Research Communications, 2003, 307:198-205).*
Vajdos et al. (Journal of Molecular Biology, 2002, 320:415-428).*
Holm et al. (Molecular Immunology, 2007:1075-1084).*
Chen et al. (Journal of Molecular Biology, 1999, 293:865-881).*
Lu et al. (Biochemical and Biophysical Research Communication, 2004, 318:507-513).*
Lu, D. et al. "Simultaneous blockade of both the epidermal growth factor rectpor and the insulin-like growth factor receptor signaling pathways in cancer cells with a fully human recombinant bispecific antibody." *Journal of Biological Chemistry* vol. 279 pp. 2856-2865 (2003).
Jendreyko, N et al. "Intrabodies, bispecific, tetravalent antibodies for the simultaneous functional knockout of two cell surface receptors." *Journal of Biological Chemistry* vol. 278 p. 47812-47819. Nov. 28, 2003.
Tournaire, R et al., "A short synthetic peptide inhibits signal transduction, migration and angiogenesis mediated by Tie2 receptor." *EMBO Reports* vol. 5, pp. 262-267. Feb. 20, 2004.
Barton, W.A. et al. "Crystal structures of the Tie2 receptor ectodomain and the angiopoietin-2-Tie2 complex." *Nature Structural & Molecular Biology* vol. 13, pp. 524-532 (Jun. 2006).
Genbank ABP52093.1 . HIL15/PAP fusion protein. Apr. 21, 2007.
Shen et al. "Single variable domain-IgG fusion. A novel recombinant approach to Fc domain-containing bispecific antibodies." *Journal of Biological Chemistry* vol. 281 pp. 10706-10714 (Feb. 15, 2006).
Helguera and Penichet. "Antibody-cytokine fusion proteins for the therapy of cancer." vol. 109; pp. 347-374 (2005).
Kim et al. "A designed angiopoietin-2 variant, pentameric COMP-Ang2, strongly activates Tie2 receptor and stimulates angiogenesis." *Biochimica et Biophysica Acta* 1793; 772-80 (Feb. 10, 2009).

(Continued)

*Primary Examiner* — Julie Wu
(74) *Attorney, Agent, or Firm* — Foley & Lardner LLP; Antoinette F. Konski

(57) ABSTRACT

The present invention relates to: a dual targeting antibody of a novel form having a water-soluble ligand fused to the N-terminus of a heavy chain or light chain of an antibody; a DNA encoding the dual targeting antibody; a recombinant expression vector containing the DNA; a host cell which is transformed with the recombinant expression vector; a method for preparing the dual targeting antibody by culturing the host cell; and a pharmaceutical composition including the dual targeting antibody.

5 Claims, 9 Drawing Sheets

Specification includes a Sequence Listing.

(56) References Cited

OTHER PUBLICATIONS

Jendreyko, N et al. "Phenotypic knockout of VEGF-R2 and Tie-2 with an itradiabody reduces tumor growth and angiogenesis *in vivo.*" *PNAS* 102; 8293-9298 (Jun. 7, 2005).
Presta, L. "Antibody Engineering for Therapeutics." *Current Opinion in Structural Biology* 13; 519-525 (Aug. 2003).
Baker, L.C.J. et al. (2016) "Acute tumour response to a bispecific Ang-2-VEGF-A antibody: insights from multiparametric MRI and gene expression profiling," British Journal of Cancer, 115:691-702.
Daly, C. et al. (2011) "REGN910, a fully-human, Ang2-specific monoclonal antibody, inhibits tumor growth as a monotherapy and dramatically potentiates the effects of VEGF Trap (aflibercept)," [Abstract] AACR, 71(6):doi 10.1158/1538-7445 AM2011-3290.
Davis, S. et al. (2003) "Angiopoetins have distinct modular domains essential for receptor binding, dimerization and superclustering," Nature Structural Biology, 10(1):38-44.
Kim, K-T. et al. (2005) "Oligomerization and Multimerization Are Critical for Angiopoeitin-1 to Bind and Phosphorylate Tie2," The Journal of Biological Chemistry, 280(20):20126-20131.
Oliner, J. et al. (2004) "Suppression of angiogenesis and tumor growth by selective inhibition of angiopoietin-2," Cancer Cell, 6:507-516.
Schliemann, C. et al. (2007) "Circulating angiopoetin is a strong prognostic factor in acute myeloid leukemia," Leukemia, 21:1901-1906.
White, R.R. et al. (2003) "Inhibition of rat corneal angiogenesis by a nuclease-resistant RNA aptamer specific for angiopoietin-2," PNAS, 100(9):5028-5033.
Zhang, Z.L. et al. (2014) "Suppression of angiogenesis and tumor growth in vitro and in vivo using an anti-angiopoietin-2 single-chain antibody," Experimental and Therapeutic Medicine, 7:543-552.

\* cited by examiner

FIG.1

CCAGCGGTGTGGGTTCC
BstXI hAng2
(F281-F496)
```
TTCAGAGACTGTGCTGAAGTATTCAAATCAGGACACACCACGAATGGCATCTA
CACGTTAACATTCCCTAATTCTACAGAAGAGATCAAGGCCTACTGTGACATGG
AAGCTGGAGGAGGCGGGTGGACAATTATTCAGCGACGTGAGGATGGCAGCGTT
GATTTTCAGAGGACTTGGAAAGAATATAAAGTGGGATTTGGTAACCCTTCAG
GAGAATATTGGCTGGGAAATGAGTTTGTTTCGCAACTGACTAATCAGCAACGC
TATGTGCTTAAAATACACCTTAAAGACTGGGAAGGGAATGAGGCTTACTCAT
TGTATGAACATTTCTATCTCTCAAGTGAAGAACTCAATTATAGGATTCACCT
TAAAGGACTTACAGGGACAGCCGGCAAAATAAGCAGCATCAGCCAACCAGGAA
ATGATTTTAGCACAAAGGATGGAGACAACGACAAATGTATCTGCAAATGTTC
ACAAATGCTAACAGGAGGCTGGTGGTTTGATGCATGTGGTCCTTCCAACTTGA
ACGGAATGTACTATCCACAGAGGCAGAACACAAATAAGTTCAACGGCATTAAA
TGGTACTACTGGAAAGGCTCAGGCTATTCGCTCAAGGCCACAACCATGATGAT
CCGACCAGCAGATTTC
```

TCAGGAGGCGGAGGTAGTGGCGGAGGAGGCTCCGGTTCC
Linker

6A6 V_L
```
AATTTTATGCTGACTCAGCCCCCCTCAGTGTCAGTGTCCCCAGGAAAGACGGC
CAGGATCACTTGTAGGGGAGATAACCTTGGAGATGTAAATGTTCACTGGTACC
AGCAGCGGCCAGGCCAGGCCCCTGTATTGGTCATGTATTATGATGCCGACCGGC
CCTCAGGGATCCCTGAGCGATTCTCTGGCTCCAACTCTGGGAACACGGCCACAC
TGACCATCAGCGGAGTCGAAGCCGGGGATGAGGCCGACTACTATTGTCAGGTG
TGGGATAGGACTAGTGAGTATGTCTTCGGAACTGGGACCAAGGTCACCGTCCT
AGGT
```

GGAGGAGCCAGCCTCGTGG
BstXI

FIG.6
1) VEFG 165 COATING
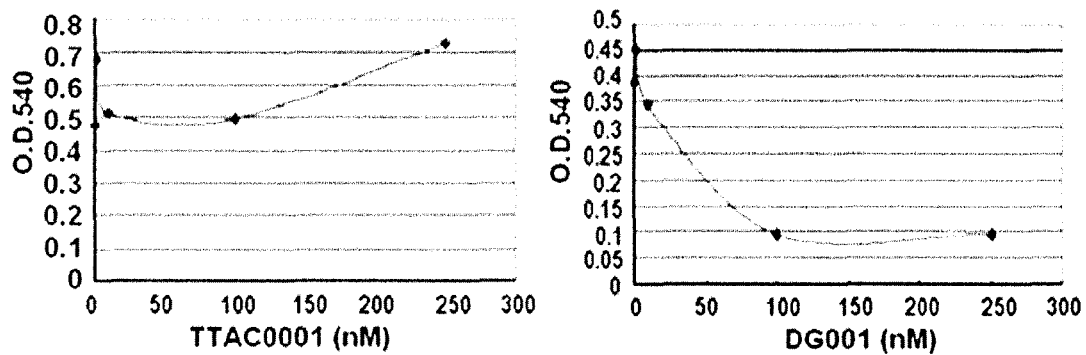
2) Ang2-Fc COATING
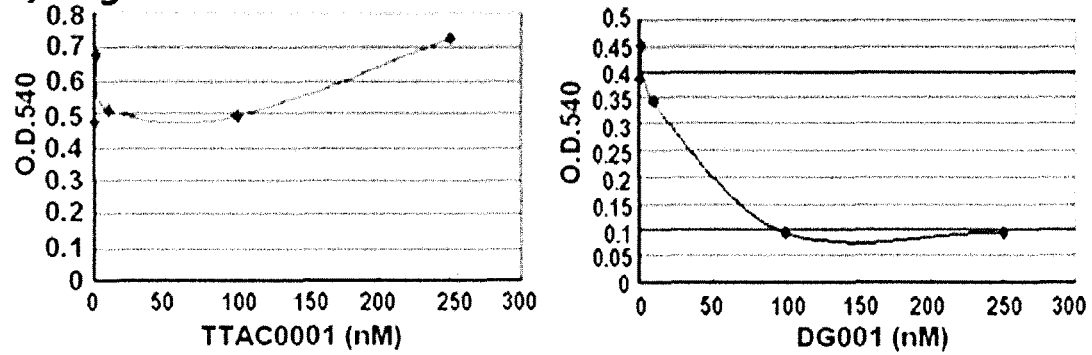

FIG.9
1) Tie-2 PHOSPHORYLATION INHIBITION ANALYSIS
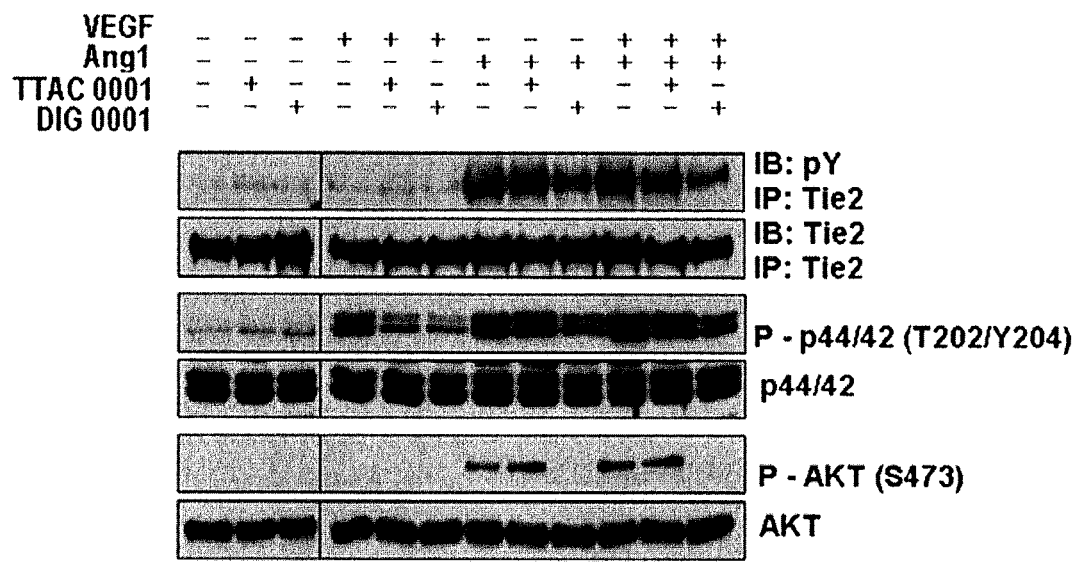
2) KDR PHOSPHORYLATION INHIBITION ANALYSIS
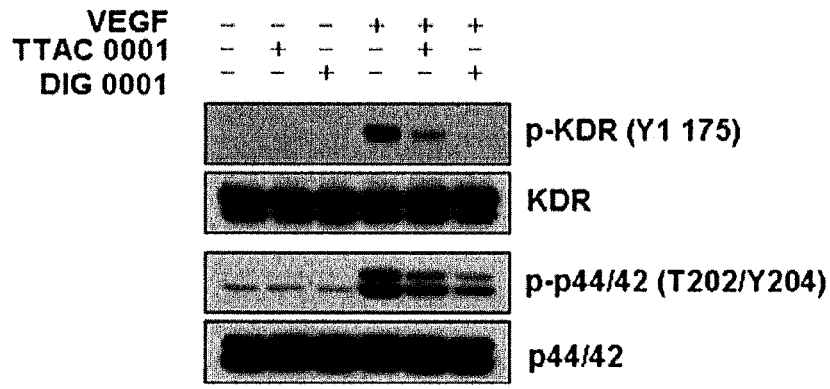

```
                           SEQUENCE LISTING

<160> NUMBER OF SEQ ID NOS: 6

<210> SEQ ID NO 1
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 1
cactccagcg gtgtgggttc cttcagagac tgtgctgaag tattc              45

<210> SEQ ID NO 2
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 2
actacctccg cctcctgaga aatctgctgg tcggatcatc atggttg             47

<210> SEQ ID NO 3
<211> LENGTH: 62
<212> TYPE: DNA
<213> ORGANISM: Artificial Sequence
<220> FEATURE:
<223> OTHER INFORMATION: Synthetic oligonucleotide

<400> SEQUENCE: 3
ggagcctcct ccgccactac ctccgcctcc tgagaaatct gctggtcgga tcatcatggt   60
tg                                                                  62

<210> SEQ ID NO 4
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 4
agtggcggag gaggctccgg ttccaatttt atgctgactc ag                 42

<210> SEQ ID NO 5
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 5
cagatctttc cacgaggctg gctcctc                                  27

<210> SEQ ID NO 6
<211> LENGTH: 1047
<212> TYPE: DNA
<213> ORGANISM: Artificial Sequence
<220> FEATURE:
<223> OTHER INFORMATION: Synthetic polynucleotide

<400> SEQUENCE: 6
```

-continued

```
ccagcggtgt gggttccttc agagactgtg ctgaagtatt caaatcagga cacaccacga    60
atggcatcta cacgttaaca ttccctaatt ctacagaaga gatcaaggcc tactgtgaca   120
tggaagctgg aggaggcggg tggacaatta ttcagcgacg tgaggatggc agcgttgatt   180
ttcagaggac ttggaaagaa tataaagtgg gatttggtaa cccttcagga gaatattggc   240
tgggaaatga gtttgtttcg caactgacta atcagcaacg ctatgtgctt aaaatacacc   300
ttaaagactg ggaagggaat gaggcttact cattgtatga acatttctat ctctcaagtg   360
aagaactcaa ttataggatt caccttaaag gacttacagg gacagccggc aaaataagca   420
gcatcagcca accaggaaat gattttagca caaaggatgg agacaacgac aaatgtatct   480
gcaaatgttc acaaatgcta acaggaggct ggtggtttga tgcatgtggt ccttccaact   540
tgaacggaat gtactatcca cagaggcaga acacaaataa gttcaacggc attaaatggt   600
actactggaa aggctcaggc tattcgctca aggccacaac catgatgatc cgaccagcag   660
atttctcagg aggcggaggt agtggcggag gaggctccgg ttccaatttt atgctgactc   720
agccccctc agtgtcagtg tccccaggaa agacggccag gatcacttgt aggggagata   780
accttggaga tgtaaatgtt cactggtacc agcagcggcc aggccaggcc cctgtattgg   840
tcatgtatta tgatgccgac cggccctcag ggatccctga gcgattctct ggctccaact   900
ctgggaacac ggccacactg accatcagcg gagtcgaagc cggggatgag gccgactact   960
attgtcaggt gtgggatagg actagtgagt atgtcttcgg aactgggacc aaggtcaccg  1020
tcctaggtgg aggagccagc ctcgtgg                                      1047
```

DUAL TARGETING ANTIBODY OF NOVEL FORM, AND USE THEREOF

CROSS REFERENCE TO RELATED APPLICATIONS

This application is the national stage entry under 35 USC 371 for PCT/KR2009/004084, filed Jul. 22, 2009, which claims the benefit of the May 20, 2009 priority date of Korean Application No. 10-2009-0044032. The contents of both the foregoing applications are incorporated herein by reference.

TECHNICAL FIELD

The present invention relates to a dual targeting antibody of a novel form having a water-soluble ligand fused to the N-terminus of a heavy chain or light chain of an antibody, a DNA encoding the dual targeting antibody, a recombinant expression vector containing the DNA, a host cell which is transformed with the recombinant expression vector, a method for producing the dual targeting antibody by culturing the host cell, and a pharmaceutical composition including the dual targeting antibody.

BACKGROUND ART

Angiogenesis refers to a mechanism by which new blood vessels are formed from the pre-existing blood vessels through the growth, differentiation and migration of endothelial cells. It is known that angiogenesis plays an important role in the normal growth process including wound healing and a woman's menstrual cycle (Risau, Nature, 386: 671, 1997) and the abnormally excessive angiogenesis plays a critical role in the growth and metastasis of tumor and the attack of diseases such as age-related macular degeneration (ARMD), diabetic retinopathy, psoriasis, rheumatoid arthritis and chronic inflammation (Carmeliet and Jain, Nature, 407: 249, 2000).

In 1971, Dr. J. Folkman proposed a hypothesis that the growth and metastasis of tumor is angiogenesis-dependent, and thus the therapeutic strategy focusing on the anti-angiogenesis may involve a new therapeutic agent for solid cancer. Thereafter, many researchers have been increasingly interested in excessive research associated with the inhibition of the angiogenesis mechanism (Ferrara and Kerbel, Nature, 435: 967, 2005). The pattern of progression of angiogenesis is determined by the general balance between angiogenesis-inducing factors and angiogenesis-inhibiting factors and takes place through complex and sequential processes of multiple steps. When referring to such a process, first, various angiogenesis-inducing factors including a vascular endothelial growth factor (VEGF) secreted from tissues with tumor or wounds bind to their corresponding receptors in the periphery of pre-existing vascular endothelial cells to activate the vascular endothelial cells, thereby increasing the permeability of the vascular endothelial cells. Moreover, proteinases such as a matrix metalloproteinase (MMP) are secreted to digest the basement membrane and extracellular matrix around the vascular endothelial cells, such that the vascular endothelial cells escape from the pre-existing capillary vessel and migrate/proliferate toward tissues secreting the angiogenesis-inducing factor. The migrating and proliferating vascular endothelial cells form a tubular structure in the blood vessel, and a stable and mature blood vessel is finally formed as a pericyte which is a structural support of the vascular endothelial cells flows into the tubular structure. In this case, it is known that angiopoietin 1 (Ang1) secreted from the vascular endothelial cells plays an important role in the influx of pericyte and the stabilization of blood vessels by binding to its receptor, Tie-2 (Suri et al., Cell, 87:1171, 1996). Meanwhile, angiopoietin 2 (Ang2) which is known to inhibit the interaction of Ang1 and Tie-2 shows similar affinity to Tie-2 compared to Ang1, and thus Ang2 can serve to competitively inhibit a phosphorylation process induced by Ang1 (Maisonpierre et al., Science, 277:55, 1997). However, it was reported that Ang2 functions to induce the phosphorylation of Tie-2 depending on the shape of cells and the experimental method (Kim et al., Oncogene, 19:4549, 2000). Also, it was reported that the blood vessel becomes unstable and the vascular endothelial cells become sensitive to stimuli such as VEGF by inhibiting the interaction between the vascular endothelial cell and pericyte at the early stage of angiogenesis (Klagsbrun and Moses, Chem. Biol., 6:R217, 1999; Veikkola and Alitalo, Semin Cancer Biol., 9:211, 1999; Carmeliet and Jain, Nature, 407:249, 2000). In particular, Ang1 is relatively widely expressed in normal tissues (Maisonpierre et al., Science, 277:55, 1997), but is poorly expressed in tumor tissues (Hayes et al., Br. J. Cancer, 83:1154, 2000). On the other hand, from the fact that Ang2 is over-expressed in cancer tissues having a high angiogenic potential or normal tissues, such as placenta, uterus and ovary, whose blood vessel remodeling actively takes place (Kong et al., Cancer Res., 61:6248, 2001; Ahmad et al., Cancer, 92:1138, 2001), it can be presumed that the onset of angiogenesis in tumor occurs as Ang2 is present at a higher content than Ang1. Therefore, it is supposed that Ang2 serves as an agonist in a Tie-2 signaling mechanism. In sum, since the signaling mechanisms of angiopoietin and Tie-2 are not clearly identified, additional studies are required to identify the signaling mechanisms. However, Ang1 and Ang2 are considered to play important and different roles in angiogenesis.

Angiopoietin includes an N-terminus domain (N-domain) consisting of approximately 50 amino acids, a coiled coil domain (C-domain) consisting of 215 amino acids, and a fibrinogen-like domain (F-domain) consisting of approximately 215 amino acids. Among them, the N- and C-domains are associated with polymerization of angiopoietin, and the F-domain is associated with binding of a receptor Tie-2 (Davis et al., Nat. Strut. Biol., 10:38, 2003). Phosphorylation required to induce signals of Tie-2 is achieved by dimerization of the receptor like other tyrosine kinase receptors. From the fact that angiopoietin should be multimerized for this purpose (Procopio et al., J. Biol. Chem., 274:30196, 1999; Schlessinger, Cell, 103:211, 2000), it is suggested that these ligands may be used as a target for new drug development using the inhibition of angiogenesis. In particular, Davis et al. argued that a minimal module of angiopoietin for the phosphorylation of Tie-2 is a tetramer as measured using a genetic engineering technique and may be used as an antagonist when the module is composed of dimmers (Davis et al., Nat. Strut. Biol., 10:38, 2003). In another study, it was reported that an Ang1 dimeric variant does not effectively perform signaling for Tie-2 (Cho et al., Proc. Natl. Acad. Sci. U.S.A., 101:5547, 2004). That is, although it was not reported that Ang1 serves as an antagonist, the inhibition of signaling for Tie-2 by modifying the oligomeric pattern of this molecule indicates that a strategy for preventing multimerization of angiopoietin may be used to hinder the Tie-2 signaling mechanism. According to the reported binding structure of angiopoietin and Tie-2, it can be seen that a Tie-2 binding site is present in angiopoietin and the binding structure between Ang1 and Tie-2 is similar to that between Ang2 and Tie-2 (Barton W. A. et al., Nat. Struct. Biol., 13:524, 2006). Therefore, the present researchers have tried to effectively inhibit angiogenesis by constructing a dual targeting antibody in which a Tie-2 binding site to angiopoietin, particularly Ang2 in the present invention, is fused to a pre-existing antibody.

Meanwhile, as another target to inhibit angiogenesis, attention has been paid to a VEGF/VEGFR signaling mechanism in the present invention. VEGF that is known to have a significant effect on most steps of an angiogenic process is widely secreted from a hypoxia site of a tumor region. In 1989, VEGF was identified by Dr. N. Ferrara, et al. of Genentech through protein isolation and purification and cDNA cloning (Leung et al., Science, 246:1306, 1989). VEGF called VEGF-A has been known to have four isotypes (VEGF121, VEGF165, VEGF189 and VEGF206). Among them, it was reported that VEGF165 is abundant in all human tissues except for the placenta (Tisher et al., J. Biol. Chem., 266:11947, 1991). It is known that VEGF binds to its receptors VEGFR-1 and VEGFR-2 with a very high affinity but induces mechanisms associated with angiogenesis such as proliferation and migration of vascular endothelial cells by transducing its signals through VEGFR-2. For this reason, VEGF and VEGFR-2 have been mainly targeted to inhibit the angiogenesis mechanisms induced by VEGF, and many articles dealing with these contents were reported (Ellis and Hicklin, Nature Rev. Cancer, 8:579, 2008; Youssoufian et al., Clin. Cancer Res., 13:5544s, 2007). For example, Avastin of Genentech is a humanized antibody targeting VEGF-A (Ferrara et al., Biochem. Biophy. Res. Comm., 333:328, 2005) and has been approved by the U.S. Food and Drug Administration (FDA) for metastatic colon cancer in 2004, non-small cell lung cancer in 2006 and Her-2 negative metastatic breast cancer in 2008, respectively, and come into the market. In recent years, extensive clinical tests on various solid tumors have been conducted to enlarge the indications. In addition, Lucentis commercially available from the same company is an antibody produced by digesting only a Fab fragment from Avastin to promote its permeability when Lucentis is injected into the retina to inhibit excessive angiogenesis under the macula which is a major condition of the senile macular degeneration (Eter et al., Biodrgus, 20:167, 2006) and was approved in 2006 by the USA FDA as a therapeutic agent to treat wet age-related macular degeneration (wet-ARMD). Another therapeutic antibody targeting VEGF is VEGF-trap of Regeneron (Holash et al., PNAS, 99:11393, 2002). This is a water-soluble "decoy receptor" obtained by fusing the second immunoglobulin domain of VEGFR-1 and the third immunoglobulin domain of VEGFR-2 with human Fc and has not been approved by the USA FDA, and its phase III trials for metastatic breast cancer, metastatic lung cancer, metastatic colon cancer and hormone-refractory prostate cancer are now under way.

Angiogenesis-inhibiting antibodies targeting a VEGF receptor VEGFR-2 include IMC-1121B (EP 1916001A2) of Imclone, CDP-791 (PCT/GB02/04619) of UCB, and TTAC-0001 (PCT/KR07/003,077) developed by the present researchers. IMC-1121B is a monoclonal antibody screened from the complete human Fab library, its phase III trials for metastatic breast cancer are now under way, and its phase III trials for gastric cancer is scheduled to be conducted in 2009. CDP-791 of UCB is a humanized antibody, and its phase II trials for non-small cell lung cancer in the form of PEGylated Di-Fab are now under way. Since this antibody does not contain an Fc domain, the antibody-dependent cell-mediated cytotoxicity or complement-dependent cytotoxicity cannot be expected. Lastly, TTAC-0001 developed by the present researchers and studied in a pre-clinical stage is a monoclonal antibody screen from the complete human ScFv library. This is only one antibody that shows reactivity to mouse- or rat-derived flk-1 (VEGFR-2 homologue) while targeting VEGFR-2 and is one of the important features differentiating from the IMC-1121B of Imclone (PCT/KR07/003,077). In particular, the cross-species cross reactivity of TTAC-0001 enables the research on an animal disease model, which helps to develop an anti-cancer agent for treatment of specific tumors in the future and to complete the related research more easily.

As such, the research aimed at the VEGF and VEGFR-2 has made great strides for the recent 5 years, and various therapeutic agents have been developed through the market and clinical studies. In addition to developing a therapeutic antibody using the inhibition of angiogenesis, many antibody therapeutic agents using a single target for each disease have been approved by the FDA and come into the market. For example, major antibody therapeutic agents leading the market of monoclonal antibodies over the world include Eribitux (Imclone) that targets an epidermal growth factor receptor (EGFR) and has been marketed as a therapeutic agent to treat metastatic colon cancer, Herceptin (Genentech) that targets Her-2/neu and has been marketed as a therapeutic agent to treat metastatic breast cancer, and Rituxan™ that targets CD-20 and has been marketed as a therapeutic agent to treat non-Hodgkin's lymphoma.

Meanwhile, according to the recent trends of the antibody market, in addition to developing an antibody having the functionality for a single target, extensive research aimed at developing a so-called dual targeting antibody (bispecific antibody) or a multi-targeting antibody (multi-specific antibody), which can have two or more targets at the same time, has been actively conducted (Van Spriel et al., Immunol. Today, 21:391, 2000; Kufer et al., Trend in Biotechnol., 22:238, 2004; Marvin and Zhu, Curr. Opin. Drug Discovery Dev., 9:184, 2006). Among these antibodies belonging to this class, there is no case in which any antibody is approved by the FDA and produced on a commercial scale. However, these antibodies have been steadily studied in laboratory and clinical levels on the basis of the continuous interests and potentials. The antibodies belonging to this class are mainly classified into (1) ScFv-based antibodies, (2) Fab-based antibodies, and (3) IgG-based antibodies, etc.

First, in the case of the ScFv-based multi-targeting antibody, there is a diabody obtained by combining VL and VH of different ScFvs and having a hybrid ScFv in a heterodimeric form (Holliger et al., Proc. Natl. Acad. Sci. U.S.A., 90:6444, 1993). However, such an antibody has a problem of poor stability due to the binding affinity to heterodimers. Also, tendem ScFv obtained by liking different ScFvs to each other (Kipriyanov et al., J. Mol. Biol., 293:41, 1999; Robinson et al., Brit. J. Cancer, 99:1415, 2008), heterodimeric ScFv obtained by expressing Jun and Fos which have a binding potentials to the termini of different ScFvs (De Kruif and Logtenberg, J. Biol. Chem., 271:7630, 1996), a heterodimeric miniantibody obtained by expressing CH1 and CL of Fab from the termini of ScFv, respectively (Muller et al., FEBS lett., 432:45, 1998), and a method for constructing a minibody in a heterodimeric ScFv form (Merchant et al., Nat. Biotechnol., 16:677, 1998) were reported. In this case, the method for constructing the minibody includes substituting some amino acids of a CH3 domain that is a homodimeric domain of Fc to change a heterodimeric structure in a "knob into hole" form and expressing these modified CH3 domains from the termini of ScFv, respectively. In addition, a variety of ScFv-based analogues were reported in the scientific literature (Kipriyanov and Le Gall, Curr. Opin. Drug Discovery Dev., 7:233, 2004), and a triple target ScFv using a triabody and a quadruple target ScFv using a tetrabody were also reported in the scientific literature (Hudson and Kortt, J. Immunol. Methods, 231:177, 1999).

Second, the Fab-based multi-targeting antibody mainly has the form of heterodimeric Fab obtained by combining separate Fab's against specific antigens with each other using a disulfide bond or a mediator (Brennan et al., Science, 229:81, 1985; Kostelny et al., J. Immunol., 148:1547, 1992). Meanwhile, it was reported that a dual targeting antibody having two antigen valencies is produced by expressing ScFvs against different antigens from the termini of a heavy chain or a light chain of specific Fab (Schoonjans et al., J. Immunol., 165:7050, 2000; Lu et al., J. Immunol. Methods, 267:213, 2002), and a dual targeting antibody is produced in a homodimeric form to have four antigen valencies by interposing a hinge region between Fab and ScFv (Coloma and Morrison, Nat. Biotechnol., 15:159, 1997). Also, a dual targeting bibody produced with three valencies for antigens by fusing ScFvs against different antigens to the termini of the light chain and heavy chain of Fab, and a triple target bibody produced with three valencies for antigens by fusing different ScFvs respectively to the termini of the light chain and heavy chain of Fab were also reported in the scientific literature (Schoonjans et al., J. Immunol., 165:7050, 2000). Also, a triple targeting antibody F(ab')3 produced in a simple shape by chemically conjugating three different Fabs was also reported (Tutt et al., J. Immunol., 147:60, 1991).

Third, in the case of the IgG-based multi-targeting antibody, a hybrid hybridoma producing a dual targeting antibody, so-called quadroma was obtained by Trion Pharma by hybridizing mouse and rat hybridomas. The dual targeting antibody Ertumaxomab (antigen: Her-2/neu, CD3) produced by this company proceeded into phase II trials for metastatic breast cancer (Kiewe and Thiel, Expert Opin. Investig. Drugs, 17:1553, 2008), and Catumaxomab (antigen: EpCAM, CD3) proceeded into phase II trials for gastric cancer and ovarian cancer and phase III trials for malignant ascites (Shen and Zhu, Curr. Opin. Mol. Ther., 10:273, 2008). However, these antibodies cannot exclude a human anti-mouse antibody (HAMA) or human anti-rat antibody (HARA) reaction caused by their repeated administration. Meanwhile, a dual targeting antibody of "Holes and Knob" produced in a heterodimeric form by modifying some amino acids of a CH3 homodimeric domain of Fc for different heavy chains while sharing a light chain domain was also reported (Merchant et al., Nat. Biotechnol., 16:677, 1998). In addition to the dual targeting antibody in a heterodimeric form, it was reported that (ScFv) 4-IgG (antigen: EGFR, IGF-1R) is expressed in a homodimeric form by fusing two different ScFvs to the constant domains of a light chain and a heavy chain of IgG instead of the variable domains thereof (Lu et al., J. Biol. Chem., 279:2856, 2004). However, this antibody has a problem of very low productivity, but the same research group produced a di-diabody with improved productivity to the same target by compensating the problem of (ScFv) 4-IgG, and confirmed its potentials (Lu et al., J. Biol. Chem., 280:19665, 2005). However, such an antibody did not overcome the problem of poor stability of the diabody. Also, Shen et al. of Imclone produced a dual targeting antibody by fusing only a single variable domain for mouse platelet-derived growth factor receptor-α (PDGFR-α) to the N-terminus of a light chain of a chimeric monoclonal antibody IMC-1C11 against human VEGFR-2, and reported its potentials (Shen et al., J. Biol. Chem., 281:10706, 2006; Shen et al., J. Immunol. Methods, 318:65, 2007). Recently, Rossi et al. proposed an antibody having multiple antigen valencies for CD20 by a method so called "dock and lock (DNL)" using a dimerization and docking domain (DDD) of an R subunit of protein kinase A (PKA) and an anchoring domain of the PKA (Rossi et al., Proc. Natl. Acad. Sci. U.S.A., 103:6841, 2006; Rossi et al., Cancer Res., 68:8384, 2008), and the same research group reported a dual targeting antibody on the basis of such a technique (Chang et al., Clin. Cancer Res., 13:5586, 2007). It is known that the antibodies using the DNL method have advantages in that they are easy to apply, can be variously combined since it is produced in a module type, and has excellent in vivo stability, but have problems in that they may be degraded by in vivo proteinase and have immunogenicity-related problems.

There are various dual targeting or multi-targeting antibodies reported in the scientific literature up to the present, and these antibodies have functional merits and demerits depending on the morphological features according to their intended uses. In particular, extensive research aimed at developing therapeutic dual targeting and multi-targeting antibodies to treat cancer has continued to progress. However, it is very important to select antigens targeted by the antibodies obtained through such research such that the antibodies can perform their proper functions.

DISCLOSURE

Technical Problem

Therefore, in order to develop a dual targeting antibody for anti-cancer treatment using angiogenesis inhibition, the present inventors have produced a dual targeting antibody, which can neutralize two receptors, VEGFR-2 and Tie-2, which are closely associated with the angiogenesis mechanism, in a new form which has not been reported until now, confirm that the antibody shows an equivalent or better anti-cancer effect even in vivo as well as on a cellular level compared to a single targeting antibody against VEGFR-2 or Tie-2, and completed the present invention.

An object of the present invention is to provide a dual targeting antibody of a novel form having a water-soluble ligand fused to the N-terminus of a heavy chain or light chain of an antibody.

Another object of the present invention is to provide a DNA encoding the dual targeting antibody.

Still another object of the present invention is to provide a recombinant expression vector containing the DNA.

Yet another object of the present invention is to provide a host cell transformed with the recombinant expression vector.

Still yet another object of the present invention is to provide a method for producing a dual targeting antibody by incubating the host cell.

A further object of the present invention is to provide a pharmaceutical composition including the dual targeting antibody.

Technical Solution

The present invention provides a dual targeting antibody of a novel form having a water-soluble ligand fused to the N-terminus of the heavy chain or light chain of an antibody.

The term "antibody" used in the description of the present invention refers to a protein molecule that is produced by B cells to specifically recognize various types of antigens and serves as an antigen receptor of the B cells. This molecule is in a Y shape, and consists of two identical light chains and two identical heavy chains. All the light chains and heavy chains include variable and constant regions. The four chains are fixed by disulfide bonds located in flexible regions of the heavy chains, which are referred to as a hinge region. The variable regions in all the heavy chains and light chains bind to each other to form two identical antigen-binding sites. The antibodies are classified into five classes by the heavy chain constant region: A(IgA), D(IgD), E(IgE), G(IgG) and M(IgM). Each class is referred to as an isotype, and has unique structural characteristics and different biological properties. The present invention includes antibodies of all isotypes, and IgG is preferably used.

Preferably, the antibody according to the present invention includes an antibody against an antigen that is specifically expressed in a neoplastic cell, a cancer stromal cell, a tumor-associated endothelial cell, a tumor-associated endothelial progenitor cell, a tumor-associated circulating endothelial cell, a circulating tumor cell, a cancer stem cell, etc., but the present invention is not limited thereto.

More particularly, the antibody according to the present invention includes an antibody against a protein expressed on the surface of a cell such as a vascular endothelial growth factor receptor-1 (VEGFR-1), a vascular endothelial growth factor receptor-2 (VEGFR-2), a vascular endothelial growth factor receptor-3 (VEGFR-3), an FMS-like tyrosine kinase 3 (FLT3), a c-FMS/colony stimulating factor 1 receptor (CSF1R), a rearranged during transfection (RET) cell, a mesenchymal-epithelial transition factor (c-Met), an epidermal growth factor receptor (EGFR), Her2/neu, HER3, HER4, fibroblast growth factor receptors (FGFRs), an insulin-like growth factor receptor (IGFR), platelet-derived growth factor receptors (PDGFRs), a stem cell factor receptor (c-KIT), a breakpoint cluster region (BCR), integrin, matrix metalloproteinases (MMPs), etc., but the present invention is not limited thereto.

In the present invention, the antibody may be a "polyclonal" or "monoclonal" antibody, and more preferably a monoclonal antibody. The monoclonal antibody refers to an antibody obtained from a substantially homogenous antibody population. That is, the individual antibodies constituting such a population are identical except for possible naturally occurring mutations that may be present in a small amount. The monoclonal antibody is highly specific to a single antigenic region. Moreover, unlike the polyclonal antibodies including different antibodies for different epitopes, each monoclonal antibody is induced against a single epitope on the antigen. It should not be interpreted that the monoclone is required to produce an antibody in any certain manner. For example, a monoclonal antibody useful in the present invention may be produced by a hybridoma method described in Kohler et al., Nature, 256:495 (1975) or produced by a recombinant DNA method (see U.S. Pat. No. 4,816,567). Also, the monoclonal antibody may, for example, be isolated from the phage antibody library by a technique described in Clackson et al., Nature, 352:624-628 (1991); Marks et al., J. Mol. Biol., 222:581-597 (1991).

The antibody of the present invention is preferably a "humanized antibody". The term "humanized antibody" refers to an antibody that includes an amino acid sequence that is partially or entirely derived from the human antibody germline by changing the sequence of an antibody having a non-human complementarity determining region (CDR). By the changing method, it is the simplest way to merely substitute a murine constant region with a constant region of a human antibody. Hence, a human/murine chimera, which may sufficiently reduce the immunogenicity as low as the pharmaceutical applications are allowable, is produced. However, it is preferred that the variable region and even CDR of the antibody are humanized by a technique known in the art. The framework region of the variable region is substituted with a corresponding human framework region while the non-human CDR is substantially maintained intact or the CDR is exchanged with a sequence derived from the human genome. An intact human antibody is produced in a genetically modified mouse whose immune system is modified to correspond to the human immune system.

The antibody of the present invention is particularly preferably a "human antibody". The human antibody is an antibody having an amino acid sequence corresponding to an amino acid sequence of an antibody produced by any technique for producing an antibody produced by a human or a human antibody. The human antibody may be produced by various techniques known in the art. According to one embodiment, the human antibody is screened from the phage library expressing a human antibody (Vaughan et al. Nature Biotechnology 14:309-314 (1996): Sheets et al. PNAS (USA) 95:6157-6162 (1998); Hoogenboom and Winter, J. Mol. Biol. 227:381 (1991); Marks et al. J. Mol. Biol. 222:581 (1991)). The human antibody may be produced by introducing a human immunoglobulin locus into a transformed animal, for example, a mouse whose endogenous immunoglobulin genes are partially or completely inactivated. During the challenge, it was observed that a human antibody was produced, that is highly similar as observed in the human in all aspects of gene rearrangement, assembly and antibody repertoire. Such methods are described in, for example, U.S. Pat. Nos. 5,545,807; 5,545,806; 5,569,825; 5,625,126; 5,633,425; and 5,661,016 and Marks et al. Biotechnology 10:779-783 (1992); Lonberg et al. Nature 368: 856-859 (1994); Morrison, Nature 368:812-13 (1994); Fishwild et al. Nature Biotechnology 14:845-51 (1996); Neuberger, Nature Biotechnology 14:826 (1996); Lonberg and Huszar, Intem. Rev. Immunol. 13: 65-93 (1995). In another method, the human antibody may be produced by immortalization of human B lymphocyte (for example, B lymphocyte may be recovered from a population, or immunized in vitro) that produces an antibody induced against a target antigen (Cole et al. Monoclonal Antibodies and Cancer Therapy, Alan R Liss, p. 77 (1985); Boerner et al. J. Immunol., 147(1):86-95 (1991); and U.S. Pat. No. 5,750, 373).

The term "water-soluble ligand" used in the description of the present invention means a part or all of a protein that specifically binds to a receptor present in a cell, particularly on the surface of a cell and shows a water-soluble property so that it can be soluble in water. For example, the water-soluble ligand includes, but not limited to, a vascular endothelial growth factor (VEGF), an epidermal growth factor (EGF), a placenta growth factor (PlGF), a fibroblast growth factor (FGF), a platelet-derived growth factor (PDGF), a hepatocyte growth factor (HGF), angiopoietin, etc.

In the dual targeting antibody of a novel form according to the present invention, the antibody and the ligand play their unique roles.

However, the dual targeting antibody can inhibit or amplify two signals at the same time, and thus it may be more effective compared to a case where one signal is inhibited or amplified. Compared to a case where each signal is treated with a signal inhibitor, a low dose may be administered, and two signals can be inhibited or amplified in the same time and space.

In the present invention, it is preferred that the antibody is fused to a water-soluble ligand via a linker. In the present invention, the term "linker" refers to a peptide fragment connecting two moieties of a fusion protein. In the present invention, a suitable linker includes a peptide having 5 to 25 amino acids, preferably 10 to 20 amino acids, and more preferably 10 to 15 amino acids. In some embodiments, the linker comprises (GGGGS [SEQ ID NO: 7])$_2$.

In order to produce the dual targeting antibody of the present invention, a nucleic acid sequence encoding the dual targeting antibody is produced. The nucleic acid sequence may be constructed by fusing the 3' terminus of a nucleic acid sequence encoding a water-soluble ligand to the 5' terminus of a nucleic acid sequence encoding a heavy chain or light chain of an antibody. In one aspect, the nucleic acid sequence encoding the dual targeting antibody fused via the linker may be obtained by designing a nucleic acid sequence of a linker to be contained in a primer and performing PCR.

A coding gene of the thus produced dual targeting antibody is ligated into a vector to prepare a recombinant expression plasmid, the plasmid is introduced into a host cell to prepare a transfectant or transformant cell, the host cell is amplified and incubated, and a dual targeting antibody is isolated and purified, thereby obtaining the desired dual targeting antibody.

In the present invention, the host cell used for expression of the dual targeting antibody may be a prokaryotic or eukaryotic cell. Also, a host cell in which a DNA is introduced at high efficiency and has high expression efficiency of the introduced DNA is generally used. Examples of the host cell include known eukaryotic and prokaryotic hosts such as *E. coli*, *Pseudomonas* spp., *Bacillus* spp., *Streptomyces* spp., bacteria and yeasts, insect cells such as *Spodoptera Frugiperda* 9 (SF9), animal cells such as a Chinese hamster ovary cell (CHO) and a mouse cell, COS1, COS7, human embryonic kidney 293 cells, African green monkey cell such as BSC 1, BSC 40 and BMT 10, and tissue-cultured human cells.

In the present invention, a variety of expression host/vector combinations may be used to express the dual targeting antibody. For example, expression vectors suitable for the eukaryotic host include SV40, bovine papillomavirus, adenovirus, adeno-associated virus, cytomegalovirus, and retrovirus. Expression vectors that may be used for the bacterial host include bacterial plasmids such as pBluescript, pGEX2T, pUC, pCR1, pBR322, pMB9 and derivatives thereof, a plasmid such as RP4 having a wider host range, λgt10 and λ11, phage DNA represented as various phage lambda derivatives such as NM989, and other DNA phages such as M13 and filamentous single-stranded DNA phage. Expression vectors useful in yeast cells include 2μ plasmid and derivatives thereof. A vector useful in insect cells is pVL941.

The transformation of a recombinant expression vector into a host cell includes, for example, DEAE-dextran mediated transfection, electroporation, transduction, calcium phosphate transfection, cationic lipid-mediated transfection, scrape loading and infection.

In the present invention, the host cell may be incubated in a suitable medium and under conditions that allows expression and/or isolation of the dual targeting antibody using small- or large-scale fermentation and shake flask incubation in a laboratory or industrial fermenter. The incubation is performed in a suitable culture medium containing carbon and nitrogen sources and inorganic salts by a known technique. The suitable medium is commercially available and, for example, may be prepared using components and their composition ratios described in the catalogue of the American Type Culture Collection (ATCC).

The dual targeting antibody may be isolated from this culture broth using methods known in the art. For example, the dual targeting antibody may be isolated from this culture broth using a conventional method including, but not limited to, centrifugation, filtration, extraction, spray drying, evaporation or precipitation. In addition, the dual targeting antibody may be purified using various methods known in the art including chromatography (i.e., ion exchange, affinity, hydrophobic and size exclusion), electrophoresis, fractionation (i.e., ammonium sulfate precipitation), SDS-PAGE or extraction.

A composition according to the present invention may be administered into specific molecules through any suitable route. The composition according to the present invention may be directly (for example, locally as injection, subcutaneous injection or local administration into tissue positions) or systemically (for example, parenterally or orally) provided to animals including a human using any suitable means. When the composition according to the present invention is given parenterally, for example, intravenously, subcutaneously, ocularly, intraperitoneally, intramuscularly, buccally, rectally, vaginally, intraorbitally, intracerebrally, intraspinally, intraventricularly, intrathecally, intracerebellarly, intravesically, intranasally, or by spraying, the composition preferably include a portion of an aqueous or physiologically compatible fluid suspension or solution. Therefore, since a carrier or an excipient is physiologically available, it should not have a negative effect on the electrolyte and/or volume balance of patients, in addition to delivery of a desired composition to the patients.

A pharmaceutical composition including the dual targeting antibody of the present invention may be formulated into an oral formulation such as powder, granule, tablet, capsule, suspension, emulsion, syrup or aerosol, sterile injectable solution, suppository, and percutaneous preparation according to the conventional methods, which may be used later. The carrier, the excipient, and the diluent that may be included in the composition may include lactose, dextrose, sucrose, sorbitol, mannitol, xylitol, erythritol, maltitol, starch, acacia gum, alginate, gelatine, calcium phosphate, calcium silicate, cellulose, methyl cellulose, amorphous cellulose, polyvinylpyrrolidone, water, methyl hydroxybenzoate, propyl hydroxybenzoate, talc, magnesium stearate and mineral oil. The composition may be formulated with a diluent or excipient such as filler, extending agent, binder, wetting agent, disintegrating agent or surfactant, when necessary.

In one aspect, the dual targeting antibody according to the present invention may be formulated into an oral solid preparation. The solid preparation for oral administration includes a tablet, a pill, a powder, a granule, a capsule or the like. Here, the solid preparation may be formulated by mixing at least one excipient, for example, starch, calcium carbonate, sucrose, lactose or gelatin with the extract. In addition to the simple excipient, lubricants such as magnesium stearate and talc may also be used.

In another aspect, the pharmaceutical composition including the dual targeting antibody according to the present invention may also be formulated into a liquid preparation for oral administration. The liquid preparation for oral administration includes suspension, liquid for internal use, emulsion, syrup, etc. Such a liquid preparation may include various excipients such as, for example, wetting agent, sweetening agent, aromatic, preservative, etc., in addition to the generally used inert diluents (for example, distilled water, ethanol, liquid paraffin).

In still another aspect, the pharmaceutical composition including the dual targeting antibody according to the present invention may be formulated into a preparation for parenteral administration, preferably intraperitoneal administration. The preparation for parenteral administration includes sterile aqueous solution, non-aqueous solvent, suspension, emulsion, lyophilized preparation, and suppository. The sterile aqueous solution that may be used herein includes a Hank's solution, a Ringer's solution or a suitable buffer solution such as physically buffered saline, and the suspension as the non-aqueous solvent that may be used herein includes vegetable oil such as propylene glycol, polyethylene glycol or olive oil, or injectable ester such as ethyl oleate. When necessary, antiseptic, stabilizing agent, wetting or emulsion, and salts and/or buffer for osmotic pressure regulation may be used. Meanwhile, in the case of the suppository, a conventional base such as Witepsol, Macrogol, Tween 61, cacao oil, laurin butter or glycerinated gelatin may be used.

The dual targeting antibody according to the present invention is most preferably DIG 0001 produced according to one embodiment of the present invention.

Based on TTAC0001 described in International Publication No. PCT/KR07/003,077, the production of the dual targeting antibody DIG 0001 according to the present invention was completed by fusing a binding domain of Ang2, which binds to Tie-2 via a specific linker, to a light chain amino-terminal region of the antibody (Examples 1 and 2).

The thus produced dual targeting antibody DIG 0001 was confirmed for immobility through methods such as SDS-PAGE and western blotting, and only an antibody, which was purified to at least 95% purity by means of fast protein liquid chromatography (FPLC) using a protein A affinity column, a SP-sepharose column or a size exclusion column, was secured for further close examination (Example 3).

The dual targeting antibody DIG 0001 purified as described above was confirmed for binding affinity to VEGFR-2 D1 to D3-Fc and Tie-2-Fc by means of a binding assay using ELISA, and a competitive assay on VEGF165 and Ang2 was performed by means of ELISA to confirm functionality as a dual targeting antibody (Example 4).

According to the present invention, through the cell viability assay on primarily cultured human umbilical vein endothelial cells (HUVEC), it was confirmed that the dual targeting antibody DIG 0001 can inhibit the viability of the HUVEC cells induced by either VEGF or Ang1, and also can effectively inhibit the viability of the HUVEC cells induced by both VEGF and Ang1 (Example 5).

Through the cell migration assay, it was confirmed that the dual targeting antibody DIG 0001 according to the present invention can inhibit the mobility of the HUVEC cells induced by either VEGF or Ang1, and also can effectively inhibit the mobility of the HUVEC cells induced by both VEGF and Ang1 (Example 6).

Through the western blotting, it was confirmed that the dual targeting antibody DIG 0001 according to the present invention can inhibit the signaling mechanism of Tie-2 induced by Ang1 and the signaling mechanism of VEGFR-2 induced by VEGF, and it was also confirmed that the dual targeting antibody DIG 0001 can inhibit the signaling mechanisms induced by the Ang1 and VEGF at the same time using the western blotting (Example 7).

In particular, it was confirmed that, when the dual targeting antibody DIG 0001 according to the present invention is administered to a glioblastoma animal model, a tumor was significantly reduced in volume (Example 8).

The above-mentioned antibody was produced using the following method. First, a DNA sequence of a binding domain of Ang2 for Tie-2, which can serve as antagonist for Tie-2, was amplified through PCR. In this case, the antibody was designed to include a linker DNA at the 3'-terminus of the amplified DNA fragment. The production of the dual targeting antibody that can specifically bind to VEGFR-2 and Tie-2 was completed by fusing the DNA fragment to the 5'-terminus of a light chain DNA sequence of TTAC0001 containing some of a linker DNA.

The dual targeting antibody DIG 0001 according to the present invention may be used to treat angiogenesis-related diseases by inhibiting the angiogenesis.

According to the present invention, the term "angiogenesis-related disease" includes, but not limited to, cancer, age-related macular degeneration, rheumatoid arthritis, diabetic retinopathy, psoriasis and chronic inflammation.

According to the present invention, the cancer includes, but not limited to, gastric cancer, liver cancer, lung cancer, thyroid cancer, breast cancer, cervical cancer, colon cancer, pancreatic cancer, rectal cancer, colorectal cancer, prostate cancer, kidney cancer, melanoma, bone metastatic cancer from the prostate cancer, ovarian cancer and blood cancer.

The dual targeting antibody according to the present invention may be administered at a sufficient amount to prevent, inhibit, or relieve progression of a tumor, for example, growth, invasion, metastasis and(or) relapse of a tumor for the purpose of therapeutic treatment of cancer patients. In order to achieve the purpose, the suitable amount is defined as a therapeutically effective amount. The effective amount for this application will depend on the severity of a disease and general states of a patient's own immune system.

A preferred content according to the present invention is in a range of 0.01 mg/kg to 100 mg/kg, and more preferably 0.1 mg/m$^2$ to 10 mg/m$^2$.

However, an optimum dose varies according to a disease to be treated, and the presence of side effects, and may be determined through conventional experiments. Administration of an antibody may be performed by periodic pill injections, or continuous intravenous or intraperitoneal injections from an external storage container (for example, a vein bag) or an internal storage container (for example, a biodegradable implant). Also, an antibody protein according to the present invention may be administered in combination with a variety of different biologically active molecules. However, an optimum combination of the antibody protein and the other molecules, an administration method, and a dose may be determined through conventional experiments on the technical level of those skilled in the art.

The composition according to the present invention may be used in combination with other therapeutic agents or mixed with the other therapeutic agents.

When tumors including human tumors are treated with the dual targeting antibody according to the present invention in combination with a chemotherapeutic agent, radiation, or an additional receptor antagonist or combinations thereof, a synergistic effect may be achieved. In other words, the tumor growth inhibition caused by the dual targeting antibody according to the present invention may be unexpectedly enhanced when used with the chemotherapeutic agent, the radiation or the additional receptor antagonist, or combinations thereof. For example, the synergistic effect may exemplified by the higher tumor growth inhibition expected from the use of the combination therapy than that expected from the treatment with the dual targeting antibody according to the present invention and the chemotherapeutic agent, the radiation or the additional receptor antagonist. Preferably, the synergistic effect is proved due to relief of cancer which was not expected to be relieved by the treatment with a combination of the dual targeting antibody of the present invention and the chemotherapeutic agent, or the additional receptor antagonist.

The dual targeting antibody of the present invention is administered before the start of chemotherapy or radiotherapy, after the start of these therapies, and before and during the start of a combination thereof, that is, the chemotherapy and/or radiotherapy, before and after the start of these therapies, during and after the start of these therapies, or before, during and after the start of these therapies. For example, the DIG 0001 antibody is generally administered 1 to 30 days, preferably, 3 to 20 days, and more preferably 5 to 12 days before the start the radiotherapy and/or chemotherapy.

Therefore, the antibody according to the present invention may be in vivo and in vitro used for the purpose of the research, prevention or treatment widely known in the art. Of course, it is apparent that the principle of the present invention described herein may be changed and modified by those skilled in the art, and such various changes and modifications may be made without departing from the scope of the present invention.

Advantageous Effects

The present invention provides a dual targeting antibody derived from a human monoclonal antibody that can effectively inhibit an angiogenesis-related signaling mechanism by neutralizing VEGFR-2 and Tie-2 receptors associated with angiogenesis at the same time, and a composition for inhibiting angiogenesis and treating cancer including the dual targeting antibody. The dual targeting antibody according to the present invention shows an excellent neutralization potential, and is also effective in treating cancer, compared to the pre-existing single targeting antibodies, by neutralizing two targets associated with the angiogenesis at the same time. For the two targets each having correlation to each other, it is possible to expect more excellent effects than the actual profit derived from the treatment with the single targeting antibody by constructing a dual targeting antibody of a novel form devised by the present inventors.

DESCRIPTION OF DRAWINGS

These and other features, aspects, and advantages of preferred embodiments of the present invention will be more fully described in the following detailed description, taken accompanying drawings. In the drawings:

FIG. 1 shows a DNA sequence (SEQ ID NO: 6) and functions of a gene inserted into a pIgGLD-mAng2-TTAC0001 lgt vector.

FIG. 6 shows the results of analyzing a competitive assay on VEGF and Ang-2-Fc using DIG 0001 by means of ELISA.

FIG. 9 shows the results demonstrating the inhibitory activity of phosphorylation of VEGFR-2 and ERK by VEGF of the dual targeting antibody DIG 0001 according to the present invention, and the inhibitory activity of phosphorylation of Tie-2, ERK and AKT by Ang1 of the same antibody.

MODE FOR INVENTION

Figure 2:
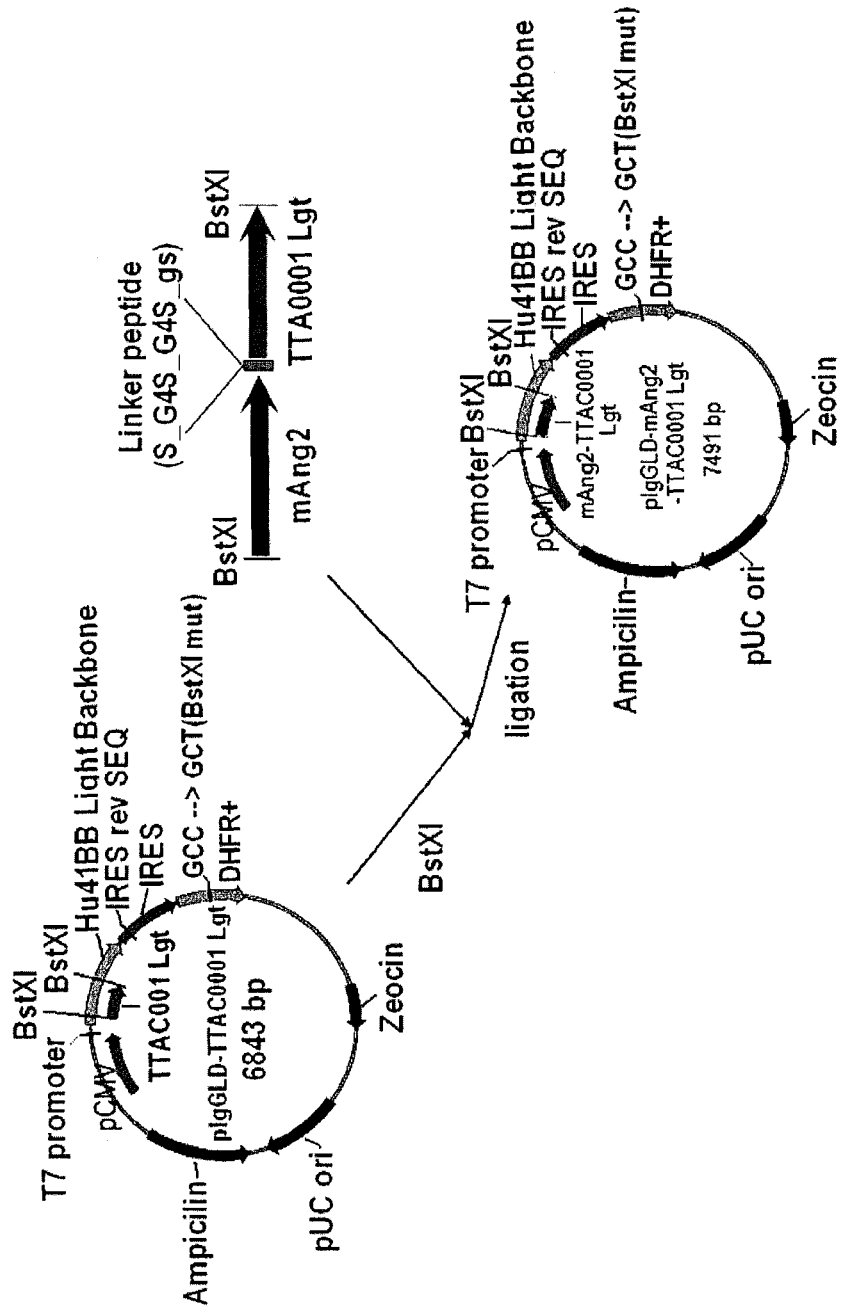
FIG. 2 schematically shows a method for constructing a pIgGLD-mAng2-TTAC0001 lgt vector according to the present invention.

Hereinafter, the following Examples will merely described to explain the present invention more specifically, and it will be made apparent to those skilled in the art to which the present invention belongs that the scope of the present invention is not limited to the Examples, depending on the purpose of the present invention.

Example 1: Construction of Expression Vector for Producing DIG 0001

A binding domain-related DNA of Ang2 binding to Tie-2 was amplified through PCR. For this purpose, a HEK293 cell line producing human Ang2-RBD (Barton et al., Structure, 13:825, 2005) was kindly provided from Dr. Dimitar B. Nikolov at the Memorial Sloan-Kettering Cancer Center in USA, and the genomic DNA was extracted, which was used as a template. In order to amplify only an Ang2 binding domain (F281-F496) from the extracted DNA, PCR was performed under the following conditions: One cycle at 94° C. for 4 minutes, 30 cycles (at 94° C. for 45 seconds/at 50° C. for 45 seconds/at 72° C. for 1 minute), one cycle at 72° C. for 7 minutes, and 4° C. for ∞. The composition of reactants used herein were as follows: 2 μl (10 pmole/μl) of a primer F-ksw001 having a BstXI restriction enzyme recognition site (5'-CAC TCCAGCGGTGTGGGT TCC TTC AGA GAC TGT GCT GAA GTA TTC, SEQ ID NO: 1), 2 μl (10 pmole/μl) of a reverse primer R'-ksw001 (5'-ACT ACC TCC GCC TCC TGA GAA ATC TGC TGG TCG GAT CAT CAT GGT TG, SEQ ID NO: 2), 1 μl (100 ng/μl) of genomic DNA used as a template DNA, 2.5 U i-Max™ II Taq (Intron #25261, Korea) used as a polymerase, 5 μl of 10× buffer, 2 μl (each 2.5 mM) of dNTP, and 37.5 μl of distilled water. The product obtained through the PCR was subjected to electrophoresis in 1% agarose gel, and a faint band below 700 bp was then isolated using a HiYield™ Gel/PCR DNA extraction kit (RBC Bioscience #YDF300, Taiwan). The PCR was re-conducted using the isolated DNA as a template to obtain an Ang2 binding domain fragment having a linker fused therein (named "mAng2"). The PCR method used herein was performed in the same manner as in the previous method, except that R-ksw001 (5'-GGA GCC TCC TCC GCC ACT ACC TCC GCC TCC TGA GAA ATC TGC TGG TCG GAT CAT CAT GGT TG, SEQ ID NO: 3) was used as a reverse primer.

Meanwhile, a light chain region of TTAC0001 used to fuse the Ang2 binding domain was amplified through PCR under the following conditions: One cycle at 94° C. for 4 minutes, 30 cycles (at 94° C. for 30 seconds/at 50° C. for 30 seconds/at 72° C. for 30 seconds), one cycle at 72° C. for 5 minutes, and at 4° C. for ∞. The composition of PCR reactants used herein were as follows: 2 μl (10 pmole/μl) of a primer F-ksw002 to which some of a linker is added (5'-AGT GGC GGA GGA GGC TCC GGT TCC AAT TTT ATG CTG ACT CAG, SEQ ID NO: 4), 2 μl (10 pmole/μl) of a primer R-ksw002 containing a BstXI restriction enzyme recognition site (5'-CAG ATC TTT CCACGAGGCTGG CTC CTC, SEQ ID NO: 5), 10 ng of pIgGLD-TTAC0001 Lgt (PCT/KR07/003,077) used as a template DNA, 2.5 U i-Max™ II Taq (Intron #25261, Korea) used as a polymerase, 5 μl of 10× buffer, 2 μl of dNTP (each 2.5 mM), and 37.5 μl of distilled water. The product obtained through the PCR was subjected to electrophoresis in 1% agarose gel, and a TTAC0001 light chain fragment corresponding to approximately 350 bp was isolated using a HiYield™ Gel/PCR DNA extraction kit (RBC Bioscience #YDF300, Taiwan) (which was named "TTAC0001 lgt").

SOE-PCR was conducted to fuse a TTAC0001 light chain region (TTAC0001_lgt) to an Ang2 fragment region (mAng2) obtained through the PCR. The PCR conditions used herein were as follows: One cycle at 94° C. for 4 minutes, 30 cycles (at 94° C. for 45 seconds/at 50° C. for 45 seconds/at 72° C. for 1 minute), one cycle at 72° C. for 7 minutes, and at 4° C. for ∞. Also, the composition of PCR reactants used herein were as follows: 2 μl (10 pmole/μl) of a primer F-ksw001 having a BstXI restriction enzyme recognition site, 2 μl (10 pmole/μl) of a primer R-ksw002, each 10 ng of mAng2 and TTAC0001 lgt as template DNAs, 2.5 U i-Max™ II Tag (Intron #25261, Korea) used as a polymerase, 5 μl of 10× buffer, 2 μl of dNTP (each 2.5 mM), 37.5 μl of distilled water. The product obtained through the PCR was subjected to electrophoresis in 1% agarose gel, and an mAng2-TTAC0001 lgt-fused PCR product corresponding to approximately 1 kb was isolated using a HiYield™ Gel/PCR DNA extraction kit (RBC Bioscience #YDF300, Taiwan) (which was named "mAng2-TTAC0001 lgt"). The isolated PCR product was inserted to a T-vector using a TOPcloner TA cloning kit (Enzymonics #EZ111, Korea), and was transformed into *Escherichia coli* DH5α. Then, the transformed *E. coli* was miniprepared, and treated with a restriction enzyme BstXI. Thereafter, a vector containing a target DNA having approximately 1 kb was outsourced and sequenced to confirm its DNA base sequence (FIG. 1 and SEQ ID NO: 6).

A method for constructing a light chain expression vector for expression of the dual targeting antibody DIG 0001 is as follows (FIG. 2). First, a TTAC0001 light chain expression vector pIgGLD-TTAC0001 Lgt (PCT/KR07/003,077) held by the present researchers was digested with BstXI, and a fragment that may be used as a vector was separated from 1% agarose gel through the electrophoresis. Also, the T-vector to which mAng2-TTAC0001 lgt was inserted was also digested with BstXI, and only a digested fragment was separated from 1% agarose gel through the electrophoresis. Thereafter, the two separated fragments was kept at the presence of a T4 DNA ligase (Enzynomics #M001S, Korea) at 4° C. for approximately 12 hours to construct one intact vector. Then, *E. coli* DH5α was transformed with the constructed vector, miniprepared, and then digested with BstXI to confirm whether or not the mAng2-TTAC0001 lgt was inserted into the constructed vector. The confirmed recombinant vector was named "pIgGLD-mAng2-TTAC0001 Lgt".

Example 2: Production and Identification of DIG 0001

Figure 3:
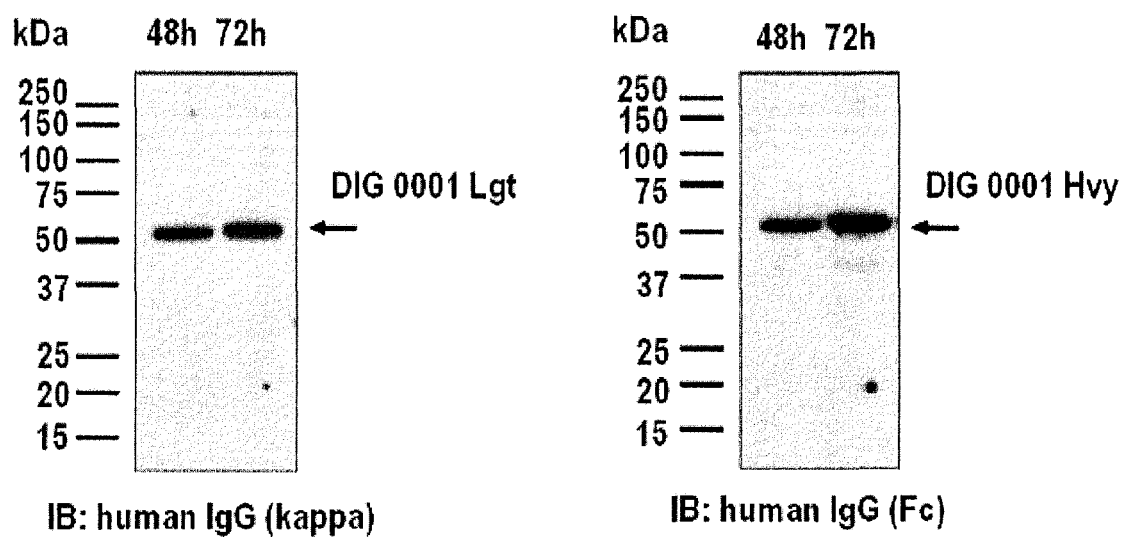
FIG. 3 shows the results obtained by randomly expressing the vector according to the present invention in CHO-DG44 cells and determining the production of a dual targeting antibody DIG 0001 through western blotting.

The constructed light chain expression vector pIgGLD-mAng2-TTAC0001 Lgt and the pre-existing heavy chain expression vector pIgGHD-TTAC0001 Hvy (PCT/KR07/003,077) was co-transduced into CHO-DG44 (dhfr-deficient CHO) cells to induce its voluntary expression, and the expression was confirmed using SDS-PAGE and western blotting. The transduction was conducted using Lipofectamine™ 2000 (Invitrogen #11668-019, USA), and its procedure was performed according to the manufacturer's instructions. In sum, $5\times10^5$ CHO-DG44 cells were inoculated into each well of a 6-well plate containing an αMEM medium (Welgene, Korea), and densely incubated until a cell density reached approximately 80 to 90% by keeping the CHO-DG44 cells at 37° C. for 24 hours in a $CO_2$ (5%) incubator with moisture. 3 μg of a recombinant vector (1.5 μg of pIgGHD-TTAC0001 Hvy and 1.5 μg of pIgGLD-mAng2-TTAC0001 Lgt) and 6 μl of Lipofectamin™ 2000 were diluted in each 250 μl of serum-free MEM media, and kept at room temperature for 5 minutes. A DNA dilute solution and a Lipofectamin™ 2000 dilute solution were mixed and reacted at room temperature for 20 minutes to form a DNA-Lipofectamin™ 2000 complex. The pre-existing medium was removed from the cultured cells, and 500 μl of the DNA-Lipofectamin™ 2000 complex and 500 μl of a serum-free αMEM medium were added to each well, and incubated at 37° C. for 6 hours in a $CO_2$ incubator. 1 ml of an αMEM medium containing 20% dialyzed fetal bovine serum was added, and incubated for 48 to 72 hours. Thereafter, only a supernatant was separated, and the expression of the antibody was confirmed using SDS-PAGE and western blotting (FIG. 3). The SDS-PAGE and western blotting were preformed according to the method widely used in the art, and the used samples were as follows: 12% SDS-polyacrylamide gel, a PVDF membrane (Millipore #IPVH00010, USA), a HRP-conjugated goat anti-human IgG (kappa) antibody, and a HRP-conjugated goat anti-human IgG (Fc) antibody (Pierce, USA).

Figure 4:
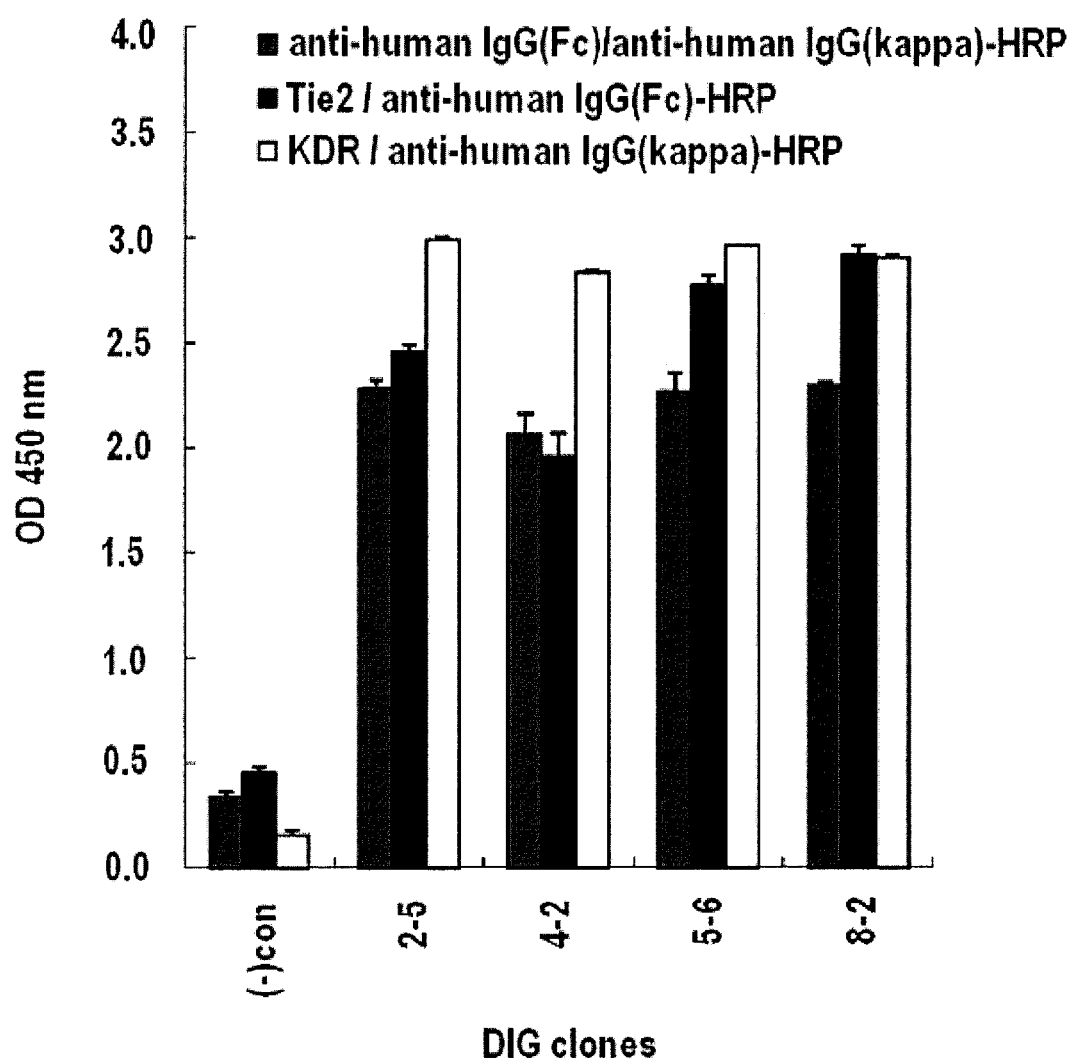
FIG. 4 shows the results of screening a high-productivity clone with repeated MTX treatment (up to 700 nM) to establish a high-productivity cell line according to the present invention.

Example 3: Establishment of Cell Line for Producing Dig 0001 and Separation and Purification of Antibody A DIG 0001-producing cell line was established using CHO-DG44 (dhfr-deficeint CHO) cells. A transduction procedure for establishing a recombinant antibody-expressing CHO-DG44 cell line was conducted in the same manner as described above. In order to screen the transduced CHO-DG44 cells (dhfr-positive), a hypoxanthine-thymidine-free αMEM medium was used, and 500 μg/ml of G418 (Sigma-aldrich, USA) and 400 μg/ml of zeocine (Invitrogen, USA) were used as selection markers to primarily screen the transduced CHO-DG44 cells. In order to obtain a monoclonal colony in which the recombinant antibody was expressed, the primarily screened cells were diluted to a density of 10 cells/ml, and inoculated in a 96-well plate (Nunc, USA). Then, the diluted cells were incubated for 2 weeks, and a single colony differentiating from a single cell was separated to establish a mother cell clone. In order to obtain a high-expression cell line, the mother cell clone was sequentially subcultured 3 to 5 times in a medium supplemented with various concentrations (40 nM, 80 nM, 160 nM, 320 nM, and 700 nM) of methotrexate (MTX), and its expression level was confirmed using ELISA. For this purpose, 2 μg/ml of a primary antibody, goat anti-human IgG (Fc) (Pierce, USA), was added at a concentration of 100 μl to the 96-well plate, and kept at 4° C. for 12 hours to complete the coating procedure. Then, a solution remaining in each well was discarded, 200 μl of a blocking solution containing 2% nonfat milk with 1×PBS was added to each well, and kept at 37° C. for 1 hour. Each well was repeatedly washed three times with a washing buffer containing 0.05% Tween-20 with 1×PBS, and 100 μl of a cell culture broth obtained from the antibody-expressing CHO-DG44 cell line was then added, and reacted at room temperature for 1 hour. Each well was washed again three times with a washing buffer, and a secondary antibody, HRP-conjugated goat anti-human IgG (kappa), was then diluted with a washing buffer at a ratio of 1:5,000, and 100 μl of the resulting antibody solution was reacted at room temperature for 1 hours. Each well was washed again three times with a washing buffer, and 100 μl of a TMB substrate reagent (BD biosciences, USA) was added, reacted for 5 to 10 minutes. Then, 50 μl of a 2N sulfuric acid ($H_2SO_4$) solution was added to stop a chromogenic reaction. An optical density (O.D) value at 450 to 650 nm was measured using a microplate reader (Tecan, Switzerland). In order to re-confirm the results, the ELISA was performed in the same manner as described above using VEGFR-2 and Tie-2 as primary antibodies and HRP-conjugated goat anti-human IgG (kappa) as a secondary antibody. Finally, a clone showing a high expression rate at 700 nM MTX was established as a high-expression cell line (FIG. 4). Incubation of the high-expression cell line was performed in an αMEM medium (Welgene, Korea) supplemented with 10% dialyzed fetal bovine serum (KDR, Korea), 100 units/ml of penicillin (Hyclone, USA) and 100 μg/ml of streptomycin (Hyclone, USA), and the cell culture was performed in a 37° C. incubator under a 5% $CO_2$ mixed air condition with moisture.

Figure 5:
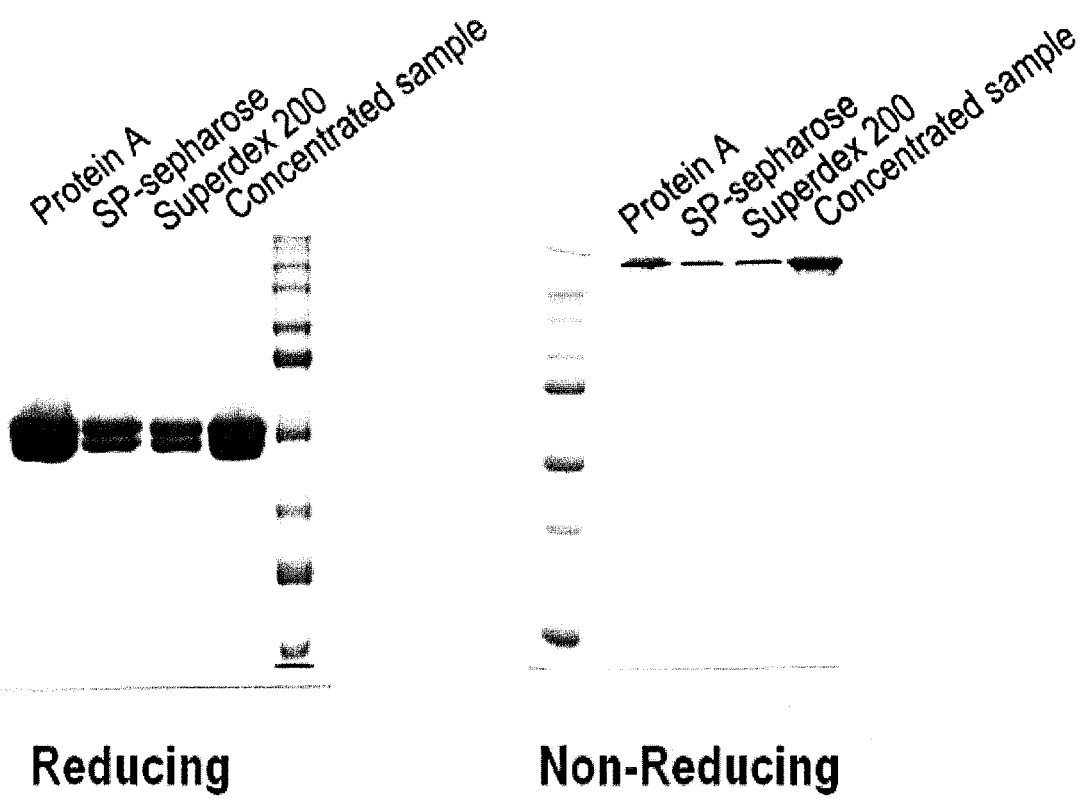
FIG. 5 shows the SDS-PAGE results of purified DIG 0001.

The dual targeting antibody DIG 0001 obtained from the incubation of the high-expression cell line was subjected to FPLC having a protein A affinity column, a SP-sepharose column or a size exclusion column to secure only an antibody, which was purified to at least 95% purity for further close examinations (FIG. 5). First, a culture broth was centrifuged to separate a cell pallet and a medium, and DIG 0001 in the separated medium was concentrated through a UF membrane (Millipore, USA) having a molecular weight cutoff of 10,000 Da or less. The medium filtered through the UF membrane was primarily purified using protein A affinity chromatography. This procedure is described in brief, as follows. The medium filtered through the UF membrane was put into a 0.1 M NaCl-containing protein A column stabilized with 20 mM sodium phosphate (pH 7.0), and an unbound protein was washed with the same buffer. Then, a protein non-specifically binding to a protein A resin was washed again with a 20 mM sodium phosphate (pH 7.0) buffer solution containing 0.5 M NaCl. A protein specifically binding to protein-A was eluted with a 0.1 M Glycine-Cl (pH 3.5) buffer containing 0.1 M NaCl, and a sample was neutralized with a 1 M Tris solution to pH 6.0. In order to prevent contamination of DNA, endotoxin and protein-A that may remain in the sample fractionated through the affinity column, cation-exchange chromatography was conducted, as follows. First, a sample eluted from a protein-A column was mixed with the same volume of a 20 mM sodium phosphate (pH 6.0) buffer. Thereafter, a SP-sepharose (5 ml, GE healthcare) column was stabilized with a 10 mM sodium phosphate (pH 6.0) buffer containing 50 mM NaCl, and a sample was added, and unbound DNA and endotoxin were washed off. Antibody molecules binding to a resin were eluted using a pH value and a salt gradient (50 mM sodium phosphate (pH 7.0), 1 M NaCl). Finally, in order to remove a multimeric antibody, the sample was put into a Superdex 200 (16 mm×60 cm, GE healthcare) column stabilized with PBS, and subjected to size exclusion chromatography. Such an antibody undergoing the purification procedure was used to conduct cellular and in vivo analysis.

Example 4: Competitive Assay of DIG 0001

A competitive assay was performed using ELISA to determine whether or not the dual targeting antibody DIG 0001 competes with VEGF and Ang2 over VEGFR-2 and Tie-2. For this purpose, each of VEGF165 and Ang2-RBD was divided at a concentration of 200 ng to a 96-well plate, and the 96-well plate was coated at room temperature for one day. Then, a reaction was performed at 37° C. for 2 hours using 2% nonfat milk/PBS. When the reaction was completed, the 96-well plate was washed with PBS, and mixture group A (obtained by mixing various concentrations (0 to 250 nM) of DIG 0001 with VEGFR-2 (ECD1-3) in which 100 ng of Fc is cut), which was reacted previously at room temperature for 1 hour, was put into each well coated with VEGF165, and reacted at room temperature for 2 hours. Then, a mixture group B (obtained by mixing various concentrations (0 to 250 nM) of DIG 0001 with 500 ng of Tie-2-Fc), which was reacted previously at room temperature for 1 hour, was put into each well, which was coated with Ang2-RBD in the same manner as described above, and reacted at room temperature for 2 hours. After the 2-hour reaction was completed, the 96-well plate was washed with PBS, 5 μg/ml of an anti-VEGFR-2 mouse antibody (Reliatech, Germany) was added as a primary reacting antibody to each well coated with VEGF165, and reacted at 37° C. for 1 hour. After each well coated with Ang2-RBD was washed with PBS, 5 μg/ml of an anti-Tie-2 mouse antibody (Abcam, England) was added as a primary antibody to each well, and reacted at 37° C. for 1 hour in the same manner as described above. Thereafter, a HRP-conjugated goat anti-mouse IgG antibody (Abcam, England) was diluted at a ratio of 1:5000, added as a secondary antibody to both wells coated with VEGF165 and Ang2-RBD, and reacted at 37° C. for 1 hour. Then, a TMB substrate reagent (BD Biosciences #555214, USA) was used to induce a chromogenic reaction, and 50 μl of a 2N sulfuric acid ($H_2SO_4$) solution was added to stop the chromogenic reaction. Measurement of the chromogenic reaction was performed at an absorbance of 450 nm and 650 nm using a microplate reader (Tecan, Switzerland) (FIG. 6).

Example 5: Survival Assay of HUVEC after Treatment with DIG 0001

Figure 7:
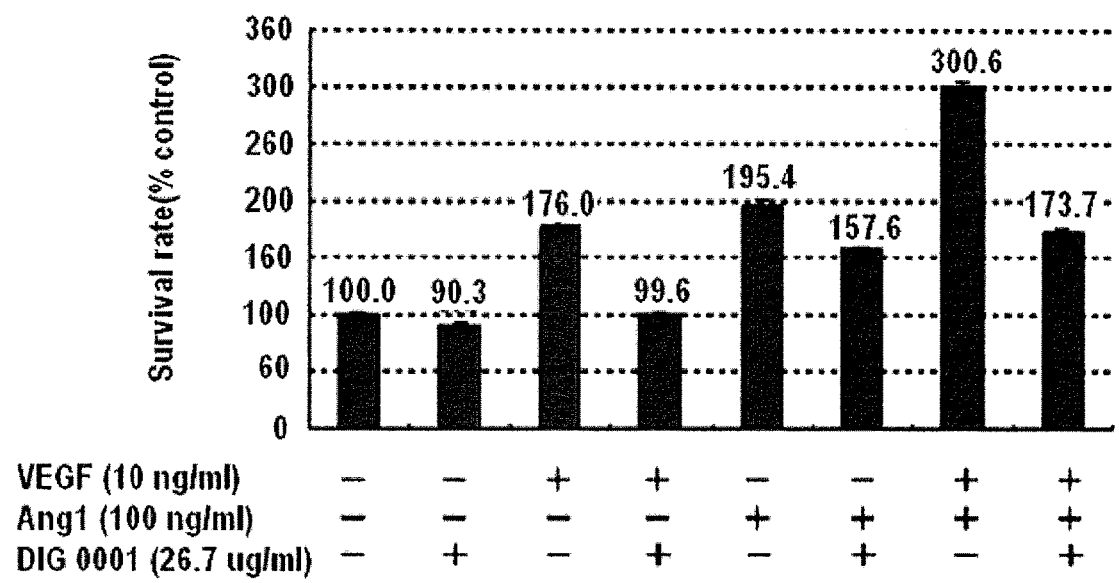
FIG. 7 shows the results of a survival assay demonstrating the viability of DIG 0001 according to the present invention on HUVEC.

In order to check a change in viability of human umbilical vein endothelial cells (HUVEC) after the treatment with DIG 0001, a cell survival assay was performed. Incubation of HUVEC was performed in a phenol red-free M199 medium (Invitrogen, USA) supplemented with 20% fetal bovine serum (Hyclone, USA), 100 units/ml of penicillin (Hyclone, USA), 100 μg/ml of streptomycin (Hyclone, USA), 3 ng/ml of a fibroblast growth factor (Upstate Biotechnology, USA), and 5 units/ml of heparin (Sigma-Aldrich, USA), and the cell culture was performed in a 37° C. incubator under a 5% $CO_2$ mixed air condition with moisture. For the survival assay of vascular endothelial cells, these cells were put into a 24-well plate and incubated for 24 until a cell density reached $2 \times 10^4$ cell/well. Thereafter, the 24-well plate was washed twice with an M199 medium, and the cells were incubated for 6 hours under a low serum concentration condition in an M199 medium supplemented with 1% fetal bovine serum (Hyclone, USA). The cells were pretreated with various concentrations of an antibody for 30 minutes, and then treated with 10 ng/ml of VEGF (R&D systems, USA) and 100 ng/ml of Ang1 (R&D systems, USA). After the 48-hour incubation, the cells were treated with WST-8 (Dojindo, Japan) for 2 hours, and an absorbance of the cell culture was measured at a wavelength of 450 nm. Then, the cell viabilities obtained under each condition were compared (FIG. 7).

Example 6: Migration Assay of HUVEC after Treatment with DIG 0001

In order to check inhibition of mobility (chemotaxis) of HUVEC on DIG 0001, a cell migration assay was performed. For the migration assay of HUVEC, an 8-μm pore-sized polycarbonate filter transwell (Corning, USA) was used.

Figure 8:
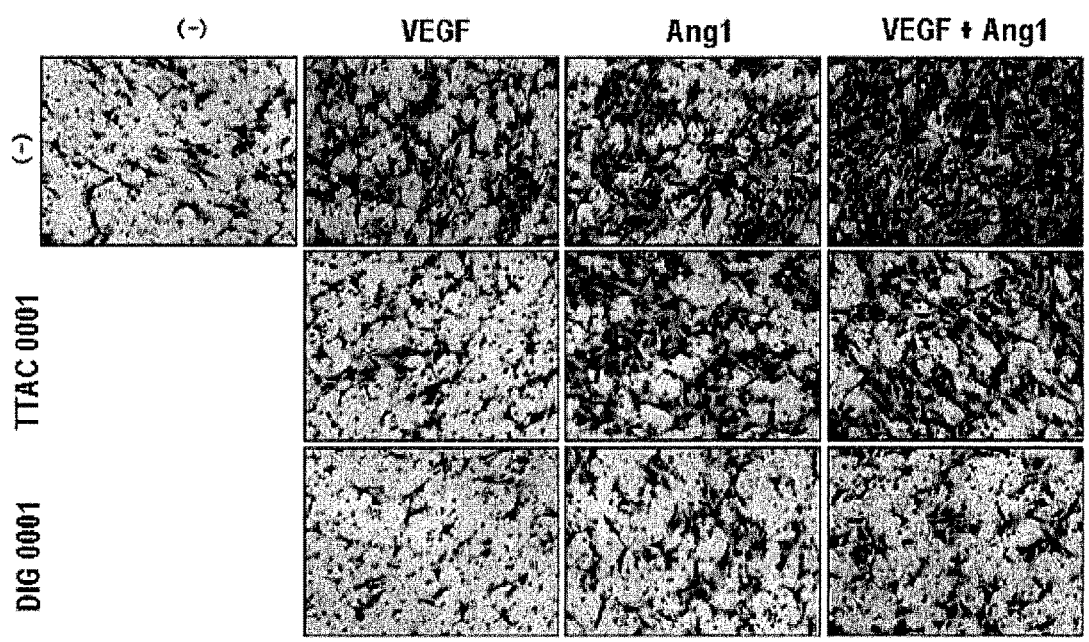
FIG. 8 shows the results of a migration assay demonstrating the mobility of DIG 0001 according to the present invention on HUVEC.

Before its use, a bottom surface of a filter was coated with 10 μg gelatin, and dried. 10 ng/ml of VEGF and 100 ng/ml of Ang1 were added to lower wells including an M199 medium supplemented with 1% fetal bovine serum. Vascular endothelial cells, which were incubated at a low serum concentration for 6 hours, were detached by treatment with trypsin, and suspended in an M199 medium supplemented with 1% fetal bovine serum until a cell density reached $1 \times 10^6$ cells/ml. The vascular endothelial cells, which were pretreated with various concentration of an antibody for 30 minutes, were uniformly sprayed at a concentration of 100 μl on an upper transwell, and incubated at 37° C. for 3.5 hours in a cell incubator. The cultured cells were stained with hematoxylin-eosin (Sigma, USA) or crystal violet (Sigma, USA), non-migrated cells attached to a top surface of a filter were removed with a swab, and migrated cells attached to a bottom surface of the filter were left. Photographs were taken of the cells with 100× magnification under an optical microscope (Olympus, IX71, Japan) equipped with a digital camera to compare the counts of the migrated cells, and 10 images obtained under each condition were calculated and analyzed (FIG. 8).

Example 7: Analysis of Inhibition of VEGFR-2 and Tie-2 Phosphorylation in Cells Using Immunoprecipitation and Western Blotting In order to check the inhibition of phosphorylation of VEGFR-2 and Tie-2 by the dual targeting antibody DIG 0001, immunoprecipitation and western blotting were performed. Vascular endothelial cells which were cultured for 24 hours were incubated for 6 hours in an M199 medium supplemented with 1% fetal bovine serum, and then pretreated with 26.7 μg/ml of DIG 0001 antibody for 30 minutes. Thereafter, the vascular endothelial cells were treated with 10 ng/ml of VEGF and 100 ng/ml of Ang1 for 15 minutes. For the analysis using immunoprecipitation, the vascular endothelial cells were washed with cold PBS, and treated with 500 μl of a buffer solution for immunoprecipitation (1% Triton X-100, 0.5% Nonidet P-40, 50 mM Tris/HCl (pH 7.4), 150 mM NaCl, 2 mM sodium orthovanadate, 2 mM EGTA, 2 mM EDTA, 1 mM phenylmethylsulfonyl fluoride, and 1 mM sodium fluoride). A solute collected with a scrapper was passed through a 26 gauge injector several times, sufficiently dissolved, and centrifuged for 10 minutes at 12,000 g to recover a supernatant. 2 μg of anti-Tie-2 (R&D systems, USA) immunoprecipitating antibody was added to 300 μg of the solute, and reacted for 8 hours. Then, a protein A/G plus agarose (Santa Cruz Biotechnology, USA) was added, and bound to the immunoprecipitating antibody. The resulting immune complex bound to the protein A/G plus agarose was centrifuged, and repeatedly washed 3 to 5 times with a buffer solution. Then, an SDS sample buffer was added, boiled, and then centrifuged to remove an agarose precipitate.

For the analysis using the western blotting, the vascular endothelial cells were treated with a lysis buffer solution (1% (w/v) SDS, 10 mM Tris (pH 7.4), 2 mM sodium orthovanadate, 2 mM EGTA, 2 mM EDTA, 1 mM phenylmethylsulfonyl fluoride, and 1 mM sodium fluoride) to obtain a solute, and the solute was boiled, and centrifuged at 4° C. at 10,000 g for 5 minutes to remove a non-soluble precipitate. A supernatant was mixed with an SDS sample buffer, and boiled for 10 minutes. The SDS-PAGE and western blotting were performed according to methods widely used in the art, and the used samples were as follows: 12% SDS-polyacrylamide Gel, a PVDF membrane (Millipore #IPVH00010, USA), an anti-Tie-2 antibody (abcam, England) and an anti-phosphotyrosine antibody (Upstate Biotechnology, USA) used as primary antibodies for analysis of Tie-2 phosphorylation inhibition activities; an anti-p44/42 antibody (Cell Signaling technology, USA) and an anti-phospho p44/42 antibody (Cell Signaling technology, USA); an anti-AKT antibody (Cell Signaling technology, USA) and an anti-phospho AKT antibody (Cell Signaling technology, USA); an anti-VEGFR-2 antibody (Cell Signaling technology, USA) and an anti-phospho VEGFR-2 antibody (Cell Signaling technology, USA) used as primary antibodies for analysis of VEGFR-2 phosphorylation inhibition activities; an anti-AKT antibody (Cell Signaling technology, USA) and an anti-phospho AKT antibody (Cell Signaling technology, USA); and an HRP-conjugated goat anti-mouse IgG antibody (Santa Cruze Biotechnology, USA) and HRP conjugated goat anti-rabbit IgG (Santa Cruze Biotechnology, USA) used as secondary antibodies binding to a primary antibody for chemiluminescence (FIG. 9).

Example 8: Tumor Growth Inhibition by DIG-0001 in Glioblastoma Animal Model

Figure 10:
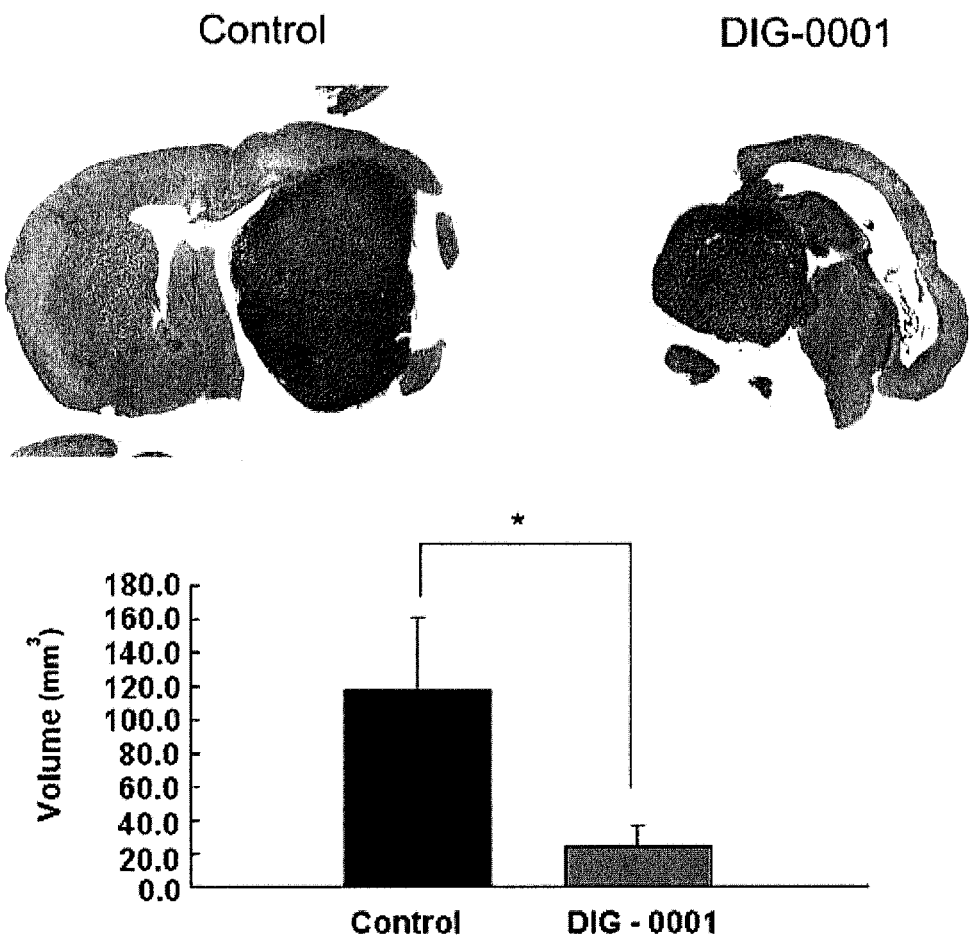
FIG. 10 shows effects of DIG 0001 according to the present invention on tumor growth inhibition in a glioblastoma mouse model.

For the growth of orthotopic glioblastoma, male Balb/c-nu mice (Japan SLC) free of a specific pathogen were used. Intracerebral transplantation of U-87MG glioblastoma ($2 \times 10^5$ cells, American Type Culture Collection) was performed according to known methods. The day after the intracerebral transplantation of the glioblastoma, the mice were divided into two groups (n=4), and treated, as follows: (a) intraperitoneal injection of PBS, and (b) intraperitoneal injection of 0.5 mg/kg of DIG-0001. All the treatments were performed 5 times (Days 15, 18, 21, 24 and 27 after inoculation of neoplastic cells). Day 29 after the transplantation of the neoplastic cells, the mice were sacrificed, their brains were removed, and coronally sectioned. One fragment was fixed with 10% buffered formalin, and embedded into formalin, and the remainders were embedded into an OCT compound. A tumor volume was obtained by measuring a volume of a fragment having the highest tumor region, and calculated according to the following equation: Width$^2 \times$ Length$\times 0.5$ (FIG. 10).

INDUSTRIAL APPLICABILITY

The composition according to the present invention can be used to treat angiogenesis-related diseases, particularly cancer.

While the preferred embodiments of the present invention have been illustrated and described, it will be understood by those of ordinary skill in the art that changes and other modifications can be made without departing from the invention in its broader aspects. Various features of the present invention are set forth in the following claims.

What is claimed is:

1. A dual targeting antibody comprising a Tie-2 binding domain of angiopoietin 2 (Ang2) fused to the N-terminus of a light chain of an antibody against VEGFR-2/KDR via a linker, wherein the antibody against VEGFR-2/KDR comprises a light chain variable domain and heavy chain variable domain comprising the amino acid sequence encoded by the nucleic acid sequence of SEQ ID NO: 6 and wherein the linker comprises (GGGGS)$_2$ (SEQ ID NO: 7).

2. A pharmaceutical composition comprising the dual targeting antibody of claim 1.

3. The pharmaceutical composition according to claim 2, wherein the pharmaceutical composition is used to treat an angiogenesis-related disease.

4. The pharmaceutical composition according to claim 3, wherein the angiogenesis-related disease is cancer.

5. The pharmaceutical composition according to claim 4, wherein the cancer is selected from the group consisting of gastric cancer, liver cancer, lung cancer, thyroid cancer, breast cancer, cervical cancer, colon cancer, pancreatic cancer, rectal cancer, colorectal cancer, prostate cancer, kidney cancer, melanoma, bone metastatic cancer of the prostate cancer, ovarian cancer, and blood cancer.

* * * * *